United States Patent
Semenov (12)

(10) Patent No.: US 9,924,873 B2
(45) Date of Patent: *Mar. 27, 2018

(54) ELECTROMAGNETIC TOMOGRAPHY SOLUTIONS FOR SCANNING HEAD

(71) Applicant: EMTensor GmbH, Vienna (AT)

(72) Inventor: Serguei Y. Semenov, Vienna (AT)

(73) Assignee: EMTensor GmbH, Vienna (AT)

( * ) Notice: Subject to any disclaimer, the term of this patent is extended or adjusted under 35 U.S.C. 154(b) by 0 days.

This patent is subject to a terminal disclaimer.

(21) Appl. No.: 15/620,182

(22) Filed: Jun. 12, 2017

(65) Prior Publication Data

US 2017/0273563 A1    Sep. 28, 2017

Related U.S. Application Data

(63) Continuation of application No. 15/159,461, filed on May 19, 2016, now Pat. No. 9,675,255, which is a
(Continued)

(51) Int. Cl.
*A61B 5/00* (2006.01)
*A61B 5/05* (2006.01)

(52) U.S. Cl.
CPC .......... *A61B 5/0073* (2013.01); *A61B 5/0042* (2013.01); *A61B 5/05* (2013.01);
(Continued)

(58) Field of Classification Search
CPC .......... A61B 2562/04; A61B 2562/046; A61B 2562/143; A61B 2576/026; A61B 5/0042;
(Continued)

(56) References Cited

U.S. PATENT DOCUMENTS

| 4,135,131 A | 1/1979 | Larsen et al. |
| 4,157,472 A | 6/1979 | Beck, Jr. et al. |

(Continued)

FOREIGN PATENT DOCUMENTS

| RU | 2449729 C2 | 5/2012 |
| WO | 9532665 | 12/1995 |

(Continued)

OTHER PUBLICATIONS

Information Disclosure Statement (IDS) Letter Regarding Common Patent Application(s), dated Dec. 7, 2017.
(Continued)

*Primary Examiner* — Michael Rozanski
(74) *Attorney, Agent, or Firm* — Tillman Wright, PLLC; James D. Wright; David R. Higgins

(57) ABSTRACT

An electromagnetic tomography system for gathering measurement data pertaining to a human head includes an image chamber unit, a control system, and a housing. The image chamber unit includes an antenna assembly defining a horizontally-oriented imaging chamber and including an array of antennas arranged around the imaging chamber. The antennas include at least some transmitting antennas and some receiving antennas. The control system causes the transmitting antennas to transmit a low power electromagnetic field that is received by the receiving antennas after passing through a patient's head in the imaging chamber. A data tensor is produced that may be inversed to reconstruct a 3D distribution of dielectric properties within the head and to create an image. The housing at least partially contains the antenna assembly and has a front entry opening into the imaging chamber. The head is inserted horizontally through the front entry opening and into the imaging chamber.

13 Claims, 34 Drawing Sheets

Related U.S. Application Data continuation of application No. 14/086,968, filed on Nov. 21, 2013, now Pat. No. 9,414,749.

(60) Provisional application No. 61/729,319, filed on Nov. 21, 2012.

(52) U.S. Cl.
CPC .......... *A61B 5/0507* (2013.01); *A61B 5/4094* (2013.01); *A61B 5/6814* (2013.01); *A61B 5/704* (2013.01); *A61B 5/0046* (2013.01); *A61B 5/6803* (2013.01); *A61B 2562/04* (2013.01); *A61B 2562/046* (2013.01); *A61B 2562/143* (2013.01); *A61B 2576/026* (2013.01)

(58) Field of Classification Search
CPC ....... A61B 5/0046; A61B 5/0073; A61B 5/05; A61B 5/0507; A61B 5/4094; A61B 5/6803; A61B 5/6814; A61B 5/704
See application file for complete search history.

(56) References Cited

U.S. PATENT DOCUMENTS

| | | | |
|---|---|---|---|
| 1,247,815 | A | 1/1981 | Larsen et al. |
| 1,638,813 | A | 1/1987 | Turner |
| 4,662,222 | A | 5/1987 | Johnson |
| 4,798,209 | A | 1/1989 | Klingenbeck et al. |
| 4,805,627 | A | 2/1989 | Klingenbeck et al. |
| 4,926,868 | A | 5/1990 | Larsen |
| 5,069,223 | A | 12/1991 | McRae |
| 5,222,501 | A | 6/1993 | Ideker et al. |
| 5,233,713 | A | 8/1993 | Murphy et al. |
| 5,263,050 | A | 11/1993 | Sutterlin et al. |
| 5,305,748 | A | 4/1994 | Wilk |
| 5,363,050 | A | 11/1994 | Guo et al. |
| 5,405,346 | A | 4/1995 | Grundy et al. |
| 5,715,819 | A | 2/1998 | Svenson et al. |
| 3,026,173 | A | 2/2000 | Svenson et al. |
| 6,026,173 | A * | 2/2000 | Svenson ............... A61B 5/05 324/637 |
| 6,073,047 | A | 6/2000 | Barsamian et al. |
| 6,332,087 | B1 | 12/2001 | Svenson et al. |
| 6,333,087 | B1 | 12/2001 | Jerdee et al. |
| 6,490,471 | B2 | 12/2002 | Svenson et al. |
| 6,503,203 | B1 | 1/2003 | Rafter et al. |
| 6,522,910 | B1 | 2/2003 | Gregory |
| 6,697,660 | B1 | 2/2004 | Robinson |
| 6,865,494 | B2 | 3/2005 | Duensing et al. |
| 7,239,731 | B1 | 7/2007 | Semenov et al. |
| 7,272,431 | B2 | 9/2007 | McGrath |
| 7,340,292 | B2 | 3/2008 | Li |
| 7,876,114 | B2 | 1/2011 | Campbell et al. |
| 8,000,775 | B2 | 8/2011 | Pogue et al. |
| 8,089,417 | B2 | 1/2012 | Popovic et al. |
| 8,207,733 | B2 | 6/2012 | Meaney et al. |
| 8,253,619 | B2 | 8/2012 | Holbrook et al. |
| 8,376,948 | B2 | 2/2013 | Brannan |
| 8,724,864 | B2 | 5/2014 | Persson et al. |
| 9,072,449 | B2 | 7/2015 | Semenov |
| 9,414,749 | B2 * | 8/2016 | Semenov ............. A61B 5/0073 |
| 9,414,763 | B2 | 8/2016 | Semenov |
| 9,414,764 | B2 | 8/2016 | Semenov |
| 9,675,254 | B2 * | 6/2017 | Semenov ............. A61B 5/0073 |
| 9,675,255 | B2 * | 6/2017 | Semenov ............. A61B 5/0073 |
| 9,724,010 | B2 | 8/2017 | Semenov |
| 2002/0017905 | A1 | 2/2002 | Conti |
| 2002/0168317 | A1 | 11/2002 | Daighighian et al. |
| 2002/0191744 | A1 | 12/2002 | Mirabelle |
| 2003/0018244 | A1 * | 1/2003 | Haddad ............... A61B 5/05 600/371 |
| 2003/0088180 | A1 | 5/2003 | Van Veen et al. |
| 2003/0090276 | A1 | 5/2003 | Weide et al. |
| 2004/0123667 | A1 | 7/2004 | McGrath |
| 2004/0174948 | A1 | 9/2004 | Kojima et al. |
| 2006/0133564 | A1 | 6/2006 | Langan et al. |
| 2006/0247531 | A1 | 11/2006 | Pogue et al. |
| 2007/0025514 | A1 | 2/2007 | Lawaczeck |
| 2007/0238957 | A1 | 10/2007 | Yared |
| 2008/0319437 | A1 * | 12/2008 | Turner ............... A61B 18/18 606/33 |
| 2009/0015832 | A1 | 1/2009 | Popovic et al. |
| 2010/0010340 | A1 | 1/2010 | Godavarty et al. |
| 2010/0067770 | A1 | 3/2010 | Persson et al. |
| 2010/0174179 | A1 | 7/2010 | Persson et al. |
| 2011/0022325 | A1 | 1/2011 | Craddock et al. |
| 2011/0263961 | A1 | 10/2011 | Craddock et al. |
| 2011/0295102 | A1 | 12/2011 | Lakkis et al. |
| 2012/0010493 | A1 | 1/2012 | Semenov |
| 2012/0083683 | A1 | 4/2012 | Kuwabara |
| 2012/0083690 | A1 | 4/2012 | Semenov |
| 2012/0172954 | A1 | 7/2012 | Zastrow et al. |
| 2012/0179037 | A1 | 7/2012 | Halmann |
| 2012/0190977 | A1 | 7/2012 | Persson et al. |
| 2014/0024917 | A1 | 1/2014 | McMahon et al. |
| 2014/0155740 | A1 | 6/2014 | Semenov |
| 2014/0275944 | A1 | 9/2014 | Semenov |
| 2014/0276012 | A1 | 9/2014 | Semenov |
| 2014/0378812 | A1 | 12/2014 | Saroka et al. |
| 2015/0257648 | A1 | 9/2015 | Semenov |
| 2015/0257649 | A1 | 9/2015 | Semenov |
| 2015/0342472 | A1 | 12/2015 | Semenov |
| 2016/0256109 | A1 | 9/2016 | Semenov |
| 2016/0262623 | A1 | 9/2016 | Semenov |
| 2016/0345856 | A1 | 12/2016 | Semenov |

FOREIGN PATENT DOCUMENTS

| | | |
|---|---|---|
| WO | 199852464 A1 | 11/1998 |
| WO | 200015109 A1 | 3/2000 |
| WO | 2005115235 A1 | 12/2005 |
| WO | 2007136334 A1 | 11/2007 |
| WO | 2008002251 A1 | 1/2008 |
| WO | 2010100649 A1 | 9/2010 |
| WO | 2011009945 A2 | 1/2011 |
| WO | 2011156810 A2 | 12/2011 |
| WO | 2011156810 A3 | 12/2011 |
| WO | 2013005134 A2 | 1/2013 |
| WO | 2013005134 A3 | 1/2013 |

OTHER PUBLICATIONS

Abubakar, A.; van den Berg, P.M. and Mallorqui, J.J. (2002). "Imaging of biomedical data using a multiplicative regularized contrast source inversion method", IEEE Transactions of Microwave Theory and Techniques 50 : 1761-1771. (10 pages).

Bulyshev, A.E.; Souvorov, A.E.; Semenov, S. Y. ; Posukh, V.G. and Sizov, Y. E. (2004). "Three-dimensional vector microwave tomography: theory and computational experiments", Inverse Problems 20 : 1239.

Bulyshev, A.E.; Souvorov, A. E.; Semenov, S.Y.; Svenson, R.H.; Nazarov, A.G.; Sizov, Y.E. and Tatsis, G. P. (2000) "Three-dimensional microwave tomography. Theory and computer experiments in scalar approximation", Inverse Problems 16 : 863.

Chew, W. C. and Wang, Y. M. (1990). "Reconstruction of two-dimensional permittivity distribution using the distorted Born iterative method", IEEE Transactions on Medical Imaging 9 : 218-225. (8 pages).

Devaney, A. J. (1992). Current research topics in diffraction tomography. In: Bertero, M. & Pike, E. (Ed.), Inverse Problems in Scattering and Imaging, Adam Hilger, New York.

Fear, Elise C., et al. "Confocal microwave imaging for breast cancer detection: Localization of tumors in three dimensions." IEEE Transactions of Biomedical Engineering 49.8 (2002): 812-822. (11 pages).

Harada, H.; Wall, D. J. N.; Takenaka, T. and Tanaka, M. (1995). "Conjugate gradient method applied to inverse scattering problem", IEEE Transactions on Antennas and Propagation 43 : 784-792. (9 pages).

(56) References Cited

OTHER PUBLICATIONS

Hawley, M.S., et al., "Microwave Imaging of Tissue Blood Content Changes," Journal of Biomedical Engineering (1991), pp. 197-202, vol. 13, No. 3, published by Butterworth-Heinermann for BES (6 pages).

Joachimowicz, N.; Mallorqui, J. J.; Bolomey, J. C. and Broquets, A. (1998). "Convergence and stability assessment of Newton-Kantorovich reconstruction algorithms for microwave tomography," IEEE Transactions on Medical Imaging 17 : 562-570. (9 pages).

Jofre, L., et al., "Medical Imaging with a Microwave Tomographic Scanner," IEEE Transactions on Biomedical Engineering (Mar. 1990), pp. 303-312, vol. 37, No. 3 (10 pages).

Kleinman, R. and den Berg, P. (1992). "A modified gradient method for two-dimensional problems in tomography," Journal of Computational and Applied Mathematics 42 : 17-35.

Lobel, P.; Kleinman, R. E.; Pichot, C.; Blanc-Feraud, L. and Bartaud, M. (1996). "Conjugate-Gradient Method for Solving Inverse Scattering with Experimental Data", IEEE Antennas and Propagation Magazine 38 : 48.

Meaney, P. M.; Paulsen, K. D.; Hartov, A. and Crane, R. K. (1996). "Microwave imaging for tissue assessment: initial evaluation in multitarget tissue-equivalent phantoms", IEEE Transactions on Biomedical Engineering 43 : 878-890. (12 pages).

Semenov, S.Y.; Posukh, V.G.; Bulyshev, A. E.; Williams, T.; Clark, P.; Sizov, Y.E.; Souvorov, A. E.; Voinov, B.A.: "Development of Microwave Tomography for Functional Cardiac Imaging." Biomedical Imaging: Macro to Nano, 2004. IEEE International Symposium on Arlington, VA, USA IEEE Apr. 15, 2004 (Apr. 15, 2004), pp. 1351-1353, XP010774114, DOI: 10.1109/ISBI.2004.1398797 ISBN: 978-0-7803-8389-0 (3 pages).

Semenov, S.Y.; Simonova, G. I.; Starostin, A.N.; Taran, M.G.; Souvorov, A.E.; Bulyshev, A.E. Svenson, R.H.; Nazarov, A.G.; Sizov, Y.E..; Posukh, V.G.; Pavlovsky, A. and Tatsis G.P. (2001) "Dielectrical Model of Cellular Structures in Radio Frequency and Microwave Spectrum. Electrically Interacting Versus Noninteracting Cells." Annals of Biomedical Engineering, vol. 29. pp. 427-435. (8 pages).

Semenov, S. Y.; Bulyshev, A. E.; Abubakar, A.; Posukh, V. G.; Sizov, Y. E.; Souvorov, A. E.; van den Berg, P. M. and Williams, T. C. (2005). Microwave-tomographic imaging of the high dielectric-contrast objects using different image-reconstruction approaches, IEEE Transactions on Microwave Theory and Techniques 53 : 2284-2294. (10 pages).

Semenov, S. Y.; Bulyshev, A. E.; Souvorov, A. E.; Svenson, R. H.; Sizov, Y. E.; Vorisov, V. Y.; Posukh, V. G.; Kozlov, I. M.; Nazarov, A. G. and Tatsis, G. P. (1998). Microwave tomography: theoretical and experimental investigation of the iteration reconstruction algorithm, IEEE Transactions on Microwave Theory and Techniques 46 : 133-141. (9 pages).

Semenov, S. Y.; Bulyshev, A. E.; Posukh, V. G.; Sizov, Y. E.; Williams, T. C. and Souvorov, A. E. (2003). Microwave Tomography for Detection/Imaging of Myocardial Infarction. I. Excised Canine Hearts, Annals of Biomedical Engineering 31 : 262-270. (9 pages).

Semenov, S., et al., "Microwave Tomography of Extremities: 1. Dedicated 2D System and Physiological Signatures," Physics in Medicine and Biology (2011), pp. 2005-2017, vol. 56, No. 7, published by Institute of Physics and Engineering in Medicine, United Kingdom (13 pages).

Semenov, S.Y.: "Microwave tomography: review of the progress towards clinical applications", Philosophical Transactions of the Royal Society, vol. 2009, No. 367, Dec. 31, 2009. pp. 3021-3042, XP002661164. DOI: 10.1098/rsta.2009.0092 the whole document. (22 pages).

Semenov, S.Y.; Kellam, J.; Althausen, P.; Williams, T.; Abubakar, A.; Bulyshev, A.; Sizov, Y. (2007) "Microwave tomography for functional imaging of extremity soft tissues: feasibility assessment." Physics in Medicine and Biology, doi: 10.1088/0031-9155/52/18/015. (15 pages).

Semenov, S.Y. et al.: "Myocardial ischemia and infarction can be detected by microwave spectroscopy. II. Biophysical reconstruction", Engineering in Medicine and Biology Society, 1996. Bridging Disciplines for Biomedicine., 18th Annual International Conference of the IEEE Amsterdam, Netherlands Oct. 31-Nov. 3, NY, NY, IEEE vol. 4 Oct. 31, 1996 pp. 1363-1364, XP010261997, DOI: 10.1109/EMBS. 1996.647455 ISBN:978-0-7803-3811-1.

Souvorov, A. E.; Bulyshev, A. E.; Semenov, S. Y.; Svenson, R. H.; Nazarov, A. G.; Sizov, Y. E. and Tatsis, G. P. (1998). Microwave tomography: a two-dimensional Newton iterative scheme, IEEE Transactions on Microwave Theory and Techniques 46 : 1654-1659. (6 pages).

Yaniv, Ziv, et al. "Electromagnetic tracking in the clinical environment." Medical physics 36.3 (2009): 876-892 (17 pages).

* cited by examiner

US 9,924,873 B2

ELECTROMAGNETIC TOMOGRAPHY SOLUTIONS FOR SCANNING HEAD

CROSS-REFERENCE TO RELATED APPLICATION

This application is a continuation of, and claims priority under 35 U.S.C. § 120 to, U.S. patent application Ser. No. 15/159,461 to Semenov, filed May 19, 2016 (the "'461 application"), which published Sep. 8, 2016 as U.S. Patent Application Publication No. 2016/0256109 A1 and issued Jun. 13, 2017 as U.S. Pat. No. 9,675,255 on Jun. 13, 2017, and which '461 application is a continuation of, and claims priority under 35 U.S.C. § 120 to, U.S. patent application Ser. No. 14/086,968 to Semenov, filed Nov. 21, 2013 (the "'968 application"), which '968 application was published Jun. 5, 2014 as U.S. Patent Application Publication No. 2014/0155740 A1 and issued on Aug. 16, 2016 as U.S. Pat. No. 9,414,749, and which '968 application is a nonprovisional patent application of, and claims priority under 35 U.S.C. § 119(e) to, U.S. provisional patent application Ser. No. 61/729,319 to Semenov, filed Nov. 21, 2012 and entitled "ELECTROMAGNETIC TOMOGRAPHY SOLUTIONS FOR SCANNING HEAD." The foregoing publication and applications are each incorporated herein by reference in their entirety. Additionally, each of the following patents, patent applications and patent application publications is incorporated by reference herein in its entirety:

(a) U.S. Pat. No. 7,239,731 to Semenov et al., issued Jul. 3, 2007 and entitled "SYSTEM AND METHOD FOR NON-DESTRUCTIVE FUNCTIONAL IMAGING AND MAPPING OF ELECTRICAL EXCITATION OF BIOLOGICAL TISSUES USING ELECTROMAGNETIC FIELD TOMOGRAPHY AND SPECTROSCOPY," which is intended, at least, to provide background and technical information with regard to the systems and environments of the inventions of the current patent application;

(b) U.S. Patent Application Publication No. 2012/0010493 A1, which was published Jan. 12, 2012 based on U.S. patent application Ser. No. 13/173,078 to Semenov, filed Jun. 30, 2011 and entitled "SYSTEMS AND METHODS OF 4D ELECTROMAGNETIC TOMOGRAPHIC (EMT) DIFFERENTIAL (DYNAMIC) FUSED IMAGING," which is intended, at least, to provide explanation of the use of "4D" technology in EMT systems, including with regard to inventions of the current patent application; and (c) U.S. Pat. No. 9,072,449 to Semenov et al., issued Jul. 7, 2015 and entitled "WEARABLE/MAN-PORTABLE ELECTROMAGNETIC TOMOGRAPHIC IMAGING," which was based on U.S. patent application Ser. No. 13/894,395 to Semenov, filed May 14, 2013 and previously published on Sep. 18, 2014 as U.S. Patent Application Publication 2014/0276012, which is intended, at least, to explain wearable and/or man-portable components of an electromagnetic tomographic imaging system.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE PRESENT INVENTION

Field of the Present Invention

The present invention relates generally to electromagnetic tomography, and, in particular but not exclusively, to electromagnetic tomography solutions for use with the heads of humans and other animals.

Background

Stroke is the 2nd leading cause of death after ischemic heart diseases, and is responsible for 4.4 million deaths (9 percent of all deaths) each year. According to American Heart Association/Stroke Association, every 40 seconds someone in America has a stroke. Every 3 minutes, someone dies of one. Stroke kills more than 137,000 Americans a year. About 795,000 Americans each year suffer a new or recurrent stroke. In Europe there are approximately 1.1 million deaths each year; in the EU there are approximately 460,000 deaths each year caused by stroke disease.

Stroke is a leading cause of serious, long-term disabilities worldwide, causing significant economic impact. The Potential Years of Life Lost (PYLL) calculated by OECD shows a significant number, which should be preventable.

Acute ischemic strokes account for about 85% of all strokes; each begins with a blood clot (thrombus) forming in the circulatory system at a site distant from the brain. The clot breaks away from this distant site forming an embolus which then travels through the circulatory system; on reaching the brain, the embolus lodges in the small vessels, interrupting blood flow to a portion of brain tissue. With this reduction in blood flow, tissue damage quickly ensues. Clinical management of stroke has been enhanced by the use of thrombolytics (clot busters) combined with the application of brain imaging techniques that reveal the pathophysiological changes in brain tissue that result from the stroke. In particular, the clinical decision to use a thrombolytic must be made within 3 hours of the onset of symptoms and requires a firm diagnosis of an ischemic stroke. This clinical decision currently relies on imaging methods such as computed tomography (CT) and magnetic resonance imaging (Mill) to reliably determine ischemic perfusion changes. Subsequent management of the stroke is enhanced by imaging the extent of the area of brain tissue with compromised blood flow. Current clinical imaging methods, including CT, positron emission tomography (PET) and MM each offer useful information on tissue properties related to perfusion, ischemia and infarction.

While each of these methods has its own advantages, none currently offers a rapid or cost effective imaging solution that can be made widely available at the "bedside" in the emergency department or to first response paramedical services. Electromagnetic tomography (EMT), on the other hand, is a relatively recent imaging modality with great potential for biomedical applications, including a non-invasive assessment of functional and pathological conditions of biological tissues. Using EMT, biological tissues are differentiated and, consequentially, can be imaged based on the differences in tissue dielectric properties. The dependence of tissue dielectric properties from its various functional and pathological conditions, such as blood and oxygen contents, ischemia and infarction malignancies has been demonstrated.

Two-dimensional (2D), three-dimensional (3D) and even "four-dimensional" (4D) EMT systems and methods of image reconstruction have been developed over the last decade or more. Feasibility of the technology for various biomedical applications has been demonstrated, for example, for cardiac imaging and extremities imaging.

As in any biomedical imaging, the classical EMT imaging scenario consists of cycles of measurements of complex signals, as scattered by a biologic object under study, obtained from a plurality of transmitters located at various points around the object and measured on a plurality of receivers located at various points around the object. This is illustrated in FIG. 1. As recounted elsewhere herein, the measured matrix of scattered EM signals may then be used in image reconstruction methods in order to reconstruct 3D distribution of dielectric properties of the object, i.e., to construct a 3D image of the object.

Generally, it is very important for image reconstruction to precisely describe a distribution of EM field with an imaging domain 21. The distribution of EM field with an imaging chamber is a very complex phenomenon, even when there is no object of interest inside.

FIG. 2 is a schematic view of a prior art EM field tomographic spectroscopic system 10, and FIG. 3 is a schematic diagram illustrating the operation of the system of FIG. 2 in a two-dimensional context. Such a system 10 could carry out functional imaging of biological tissues and could also be used for a non-invasive mapping of electrical excitation of biological tissues 19 using a sensitive (contrast) material (solution or nanoparticles) injected into the biological tissue 19 or carried in the circulation system, characterized by having dielectric properties that are a function of electrical field, generated by biological excited tissue 19. As illustrated in FIG. 2, the system 10 included a working or imaging chamber 12, a plurality of "EM field source-detector" clusters 26, an equal number of intermediate frequency ("IF") detector clusters 28, and a control system (not shown). Although only two EM field source-detector clusters 26 and two IF detector clusters 28 are shown, a much larger number of each are actually used.

The imaging chamber 12 is a watertight vessel of sufficient size to accommodate a human body or one or more parts of a human body together with a matching liquid. The imaging chamber 12 and its EM field clusters 26, as well as the IF detector clusters 28, have sometimes been mounted on carts in order to permit the respective components to be moved if necessary, and the carts may then be locked in place to provide stability.

Oversimplified, the system 10 operates as follows. An object of interest (e.g., biological tissue) is placed in the imaging domain 21. The transmitting hardware generates electromagnetic (EM) radiation and directs it to one of the antennas. This antenna transmits electromagnetic waves into imaging domain 21, and all of the other antennas receive electromagnetic waves that have passed through some portion of the imaging domain 21. The receiving hardware detects the resulting signal(s), and then the same cycle is repeated for the next antenna and the next one until all antennas have served as a transmitter. The end result is a matrix of complex data which is transmitted to one or more computers in the control system that process the data to produce an image of the object 19 in the imaging domain 21. An algorithm called an "inversion" algorithm is utilized in this process.

Electromagnetic tomography uses non-ionizing electromagnetic radiation to differentiate between human tissues. Using a compact antenna design, it creates a low power EM field (less than used in cellular phones), which interacts with the biological object and is then measured by sensors. Special imaging algorithms are then used to inverse a "data tensor" and reconstruct a 3D distribution of dielectric properties within a biological subject inside the EM field—i.e. to obtain a so-called "image tensor" or, simply, an image of the object. These imaging algorithms are in very general terms similar to the ones used in classical imaging methods (such as back-projection method used in Computed Tomography (CT)). However, the wave nature of propagation of EM waves needs to be accounted for in imaging algorithms, significantly complicating them. In addition, EMT imaging of the brain presents a significant challenge, as the brain is an object of interest that is located inside a high dielectric contrast shield, comprising the skull (with low dielectric contrast ($\in$~10-15) and cerebral spinal fluid (with high $\in$~55-60)).

The images are possible due to the contrast in dielectric properties of various tissues. The contrasts in dielectric properties can also be mapped between normal tissues and tissues under different functional or pathological conditions (functional contrasts). Examples include: malignancies in breast, liver and lung; tissue blood content/flow; hypoxia; ischemia; infarction; compartmental injury; stroke; and brain trauma.

Unfortunately, existing EMT solutions are not well-suited for certain applications. In this regard, FIGS. 4 and 5 are schematic illustrations of two three-dimensional settings for the system of FIG. 2. As evident therefrom, conventional EMT imaging chambers are oriented vertically so as to hold the matching liquid. Such an arrangement makes it very difficult to use the technology to image a human head because of the inconvenience of positioning a patient's head in the imaging chamber. This is particularly problematic in the emergency setting, where a patient may not be capable of positioning himself in an arrangement that allows him to insert his head into the imaging chamber. As a result, current implementations of EMT technology are not very suitable for use in diagnosing or treating stroke. Thus, a need exists for a safe, portable and cost-effective supplement to current imaging modalities for acute and chronic assessment of cerebral vascular diseases, including stroke. In particular, a need exists for the use of EMTensor technology in a mobile setting, such as in an ambulance or helicopter, and continual, safe and cost effective monitoring of an efficacy of treatment in ICUs and other medical facilities.

SUMMARY OF THE PRESENT INVENTION

Broadly defined, the present invention according to one aspect is an electromagnetic tomography (EMT) system for imaging a human head, as shown and described.

Broadly defined, the present invention according to another aspect is an electromagnetic tomography (EMT) system for imaging a human head, including: an integrated scanning apparatus; and a hub computer system.

In a feature of this aspect, the integrated scanning apparatus includes an imaging chamber. In a further feature, the imaging chamber is vertically oriented such that a human head may be inserted horizontally into the imaging chamber.

In another feature of this aspect, the integrated scanning apparatus houses a plurality of rings of antennas. In further features, each ring of the plurality of rings is vertically oriented; the rings of the plurality of rings are concentric with each other; and/or the rings include a first set of rings of antennas that are transmitting and receiving antennas, and a second set of rings of antennas that are receiving antennas only.

In further features pertaining to the first and second sets of rings, the second set of rings is divided into two subsets, and the first set of rings of antennas is located between the two subsets; the first subset of rings includes one ring; and/or the second subset of rings includes four rings.

In a further feature pertaining to the rings, each ring includes 32 antennas.

In another feature of this aspect, the integrated scanning apparatus is man-portable.

In another feature of this aspect, the integrated scanning apparatus and hub computer system are transportable. In a further feature, the integrated scanning apparatus and hub computer system are mobile.

Broadly defined, the present invention according to another aspect is an integrated scanning apparatus for imaging a human head in an electromagnetic tomography (EMT) system, as shown and described.

Broadly defined, the present invention according to another aspect is an integrated scanning apparatus for imaging a human head in an electromagnetic tomography (EMT) system, including: a housing defining a vertically oriented imaging chamber in which a human head may be inserted horizontally; and an array of antennas.

In a feature of this aspect, the integrated scanning apparatus is transportable. In a further feature, the integrated scanning apparatus is mobile. In a still further feature, the integrated scanning apparatus is man-portable.

In another feature of this aspect, the array of antennas is arranged in a plurality of rings of antennas. In further features, the rings of the plurality of rings are concentric with each other; the rings include a first set of rings of antennas that are transmitting and receiving antennas, and a second set of rings of antennas that are receiving antennas only; and/or each ring includes 32 antennas.

In further features pertaining to the first and second sets of rings, the second set of rings is divided into two subsets, and the first set of rings of antennas is located between the two subsets; the first subset of rings includes one ring; and/or the second subset of rings includes four rings.

Broadly defined, the present invention according to another aspect is a wearable scanning apparatus for imaging a human head in an electromagnetic tomography (EMT) system, as shown and described.

Broadly defined, the present invention according to another aspect is a method of treating a stroke patient using an electromagnetic tomography (EMT) system, as shown and described.

Broadly defined, the present invention according to another aspect is a method of treating a stroke patient using an electromagnetic tomography (EMT) system, including: in response to an emergency report and request from or on behalf of stroke patient, providing an ambulance equipped with a scanning apparatus for imaging a human head in an electromagnetic tomography (EMT) system; placing the scanning apparatus on or around the stroke patient's head; carrying out an EMT scanning process; providing data from the EMT scanning process to a hub computer system; producing EMT image results based on the provided data; and providing the EMT image results to a medical practitioner at a treatment center for use in diagnosing or treating the stroke patient upon the patient's arrival at the treatment center.

Broadly defined, the present invention according to another aspect is an image chamber unit for gathering measurement data pertaining to a human head in an electromagnetic tomography (EMT) system, including: an antenna assembly at least partially defining a horizontally-oriented imaging chamber and including an array of antennas arranged around the imaging chamber, the array of antennas including at least some transmitting antennas and at least some receiving antennas, wherein the transmitting antennas transmit a low power electromagnetic field, wherein the receiving antennas receive the low power electromagnetic field after passing through a human head in the imaging chamber and provide corresponding signals to a control system so as to produce a data tensor that may be inversed to reconstruct a 3D distribution of dielectric properties within the human head and thereby to create an image of the object; and a housing, at least partially containing the antenna assembly, having a front entry opening into the imaging chamber. The head of a human patient may be inserted horizontally through the front entry opening and into the imaging chamber.

In a feature of this aspect the antenna assembly includes a plurality of antenna disks, each antenna disk including an array of antennas. Each antenna disk includes a center opening, wherein the imaging chamber is at least partially defined by the plurality of center openings. The antenna disk center openings are circular and collectively define a cylindrical portion of the imaging chamber. The antenna assembly further includes a back disk attached to a rear of the antenna disks, wherein the back disk closes and defines a rear of the horizontally-oriented imaging chamber.

In a further feature, the array of antennas on each antenna disk is arranged in a ring whose center axis is oriented horizontally. The rings include a first set of rings of antennas that are transmitting and receiving antennas, and a second set of rings of antennas that are receiving antennas only. The second set of rings is divided into two subsets, and wherein the first set of rings of antennas is located between the two subsets. The first subset of rings includes one ring. The second subset of rings includes four rings. Each ring includes 32 antennas.

In another feature of this aspect, the image chamber unit further includes a flexible membrane separating a front portion of the imaging chamber from a rear portion of the imaging chamber. The flexible membrane conforms to a portion of the shape of a human head when the human head is inserted through the front entry opening and into the front portion of the imaging chamber. The rear portion of the imaging chamber is filled with a liquid. The liquid is a matching liquid for an electromagnetic tomography operation. The matching liquid is a mixture of glycerol, water and brine. The antenna assembly further includes a back disk attached to a rear of a plurality of antenna disks, and wherein the back disk includes at least one inlet for pumping the matching liquid into the rear portion of the imaging chamber. In a further feature of this aspect the image chamber unit of, further includes a catch basin disposed adjacent the entry opening so as to receive liquid leaking from the front of the imaging chamber. The catch basin includes a drain tube. In a further feature of this aspect the image chamber further includes a sanitary protective cap disposed in front of and against the flexible membrane to provide sanitary protection for a human head when the human head is inserted into the front entry opening and against the membrane. In yet a further feature of this aspect the image chamber further includes a protective ring around the entry opening to protect the human head from injury when inserting the head through the entry opening.

Broadly defined, the present invention according to another aspect is an electromagnetic tomography (EMT) system for gathering measurement data pertaining to a human head, including: an image chamber unit including an antenna assembly at least partially defining a horizontally-oriented imaging chamber and including an array of antennas arranged around the imaging chamber, the array of antennas including at least some transmitting antennas and at least some receiving antennas, a control system that causes the transmitting antennas to transmit a low power electromagnetic field that is received by the receiving antennas after passing through a human head in the imaging chamber and produces a data tensor from resulting signals that may be inversed to reconstruct a 3D distribution of dielectric properties within the human head and thereby to create an image of the object; and a housing, at least partially containing the antenna assembly, having a front entry opening into the imaging chamber. The head of a human patient may be inserted horizontally through the front entry opening and into the imaging chamber.

In a feature of this aspect the antenna assembly includes a plurality of antenna disks, each antenna disk including an array of antennas. Each antenna disk includes a center opening, wherein the imaging chamber is at least partially defined by the plurality of center openings. The antenna disk center openings are circular and collectively define a cylindrical portion of the imaging chamber. The antenna assembly further includes a back disk attached to a rear of the antenna disks, wherein the back disk closes and defines a rear of the horizontally-oriented imaging chamber. In a feature of this aspect, the array of antennas on each antenna disk is arranged in a ring whose center axis is oriented horizontally. The rings include a first set of rings of antennas that are transmitting and receiving antennas, and a second set of rings of antennas that are receiving antennas only. The second set of rings is divided into two subsets, and wherein the first set of rings of antennas is located between the two subsets. The first subset of rings includes one ring. The second subset of rings includes four rings. Each ring includes 32 antennas.

In another feature, the image chamber unit further includes a flexible membrane separating a front portion of the imaging chamber from a rear portion of the imaging chamber. The flexible membrane conforms to a portion of the shape of a human head when the human head is inserted through the front entry opening and into the front portion of the imaging chamber. The rear portion of the imaging chamber is filled with a liquid. The liquid is a matching liquid for an electromagnetic tomography operation. The matching liquid is a mixture of glycerol, water and brine. The antenna assembly further includes a back disk attached to a rear of a plurality of antenna disks, and wherein the back disk includes at least one inlet for pumping the matching liquid into the rear portion of the imaging chamber. In a further feature of this aspect the image chamber unit of, further includes a catch basin disposed adjacent the entry opening so as to receive liquid leaking from the front of the imaging chamber. The catch basin includes a drain tube. The catch basin is attached to the image chamber unit. The catch basin is separate from, but positioned next to, the image chamber unit.

In a further feature of this aspect the image chamber further includes a sanitary protective cap disposed in front of and against the flexible membrane to provide sanitary protection for a human head when the human head is inserted into the front entry opening and against the membrane. In yet a further feature of this aspect the image chamber further includes a protective ring around the entry opening to protect the human head from injury when inserting the head through the entry opening.

In another feature, the electromagnetic tomography (EMT) system further included a patient support. The patient support includes a headrest extending therefrom so as to position and/or orient a patient's head within the imaging chamber. The image chamber unit is disposed on top of the patient support, on one end thereof, and wherein the control system is carried beneath the patient support.

In another feature, the electromagnetic tomography (EMT) system further included a hydraulic system supplying liquid to the imaging chamber. The hydraulic system includes a holding tank for the liquid and a pump. The holding tank is a first tank, wherein the hydraulic system further includes a second internal tank, and wherein the liquid flows from the first tank to the imaging chamber and from the imaging chamber to the second tank. In a further feature of this aspect an inline valve is disposed between the first tank and the imaging chamber. In a further feature of this aspect a backflow valve is disposed between the imaging chamber and the second tank. In a further feature of this aspect a check valve is disposed between the imaging chamber and the second tank in parallel with the backflow valve. In a further feature of this aspect a temperature sensor is disposed at an inlet to the imaging chamber. A heater to raise the temperature of the liquid based on the status of the temperature sensor. A liquid sensor that prevents heating if liquid is not present in the second tank. In a further feature of this aspect, the electromagnetic tomography (EMT) system includes an overflow path from the second tank. The overflow path connects the second tank back to the first tank. The pump includes a remote control. The pump is a bi-directional pump.

Broadly defined, the present invention according to another aspect is an image chamber unit for gathering measurement data pertaining to a human head in an electromagnetic tomography (EMT) system, including: an antenna assembly at least partially defining a imaging chamber and including an array of antennas arranged around the imaging chamber, the array of antennas including at least some transmitting antennas and at least some receiving antennas, wherein the transmitting antennas transmit a low power electromagnetic field, wherein the receiving antennas receive the low power electromagnetic field after passing through a human head in the imaging chamber and provide corresponding signals to a control system so as to produce a data tensor that may be inversed to reconstruct a 3D distribution of dielectric properties within the human head and thereby to create an image of the object; a housing, at least partially containing the antenna assembly, having an entry opening into the imaging chamber; a flexible membrane separating a first portion of the imaging chamber from a second portion of the imaging chamber. The head of a human patient may be inserted through the front entry opening and into the imaging chamber.

In a feature of this aspect the imaging chamber is horizontally-oriented, wherein the entry opening is a front entry opening, wherein the first portion of the imaging chamber is at a front of the imaging chamber near the front entry opening, and wherein the second portion of the imaging chamber is at a rear of the imaging chamber such that the flexible membrane separates the front portion of the imaging chamber from the rear portion of the imaging chamber. The flexible membrane conforms to a portion of the shape of a human head when the human head is inserted through the front entry opening and into the front portion of the imaging chamber. the rear portion of the imaging chamber is filled with a liquid. The liquid is a matching liquid for an electromagnetic tomography operation. The matching liquid is a mixture of glycerol, water and brine.

In a further feature the antenna assembly further includes a back disk attached to a rear of a plurality of antenna disks, and wherein the back disk includes at least one inlet for pumping the matching liquid into the rear portion of the imaging chamber.

In a further feature the image chamber unit further includes a catch basin disposed adjacent the entry opening so as to receive liquid leaking from the front of the imaging chamber. The catch basin includes a drain tube. In a further feature of this aspect the image chamber further includes a sanitary protective cap disposed in front of and against the flexible membrane to provide sanitary protection for a human head when the human head is inserted into the front entry opening and against the membrane.

In a further feature the antenna assembly includes a plurality of antenna disks, each antenna disk including an array of antennas. Each antenna disk includes a center opening, wherein the imaging chamber is at least partially defined by the plurality of center openings. The antenna disk center openings are circular and collectively define a cylindrical portion of the imaging chamber. The antenna assembly further includes a back disk attached to a rear of the antenna disks, wherein the back disk closes and defines a rear of the horizontally-oriented imaging chamber. The array of antennas on each antenna disk is arranged in a ring whose center axis is oriented horizontally The rings include a first set of rings of antennas that are transmitting and receiving antennas, and a second set of rings of antennas that are receiving antennas only. The second set of rings is divided into two subsets, and wherein the first set of rings of antennas is located between the two subsets. The first subset of rings includes one ring. The second subset of rings includes four rings. Each ring includes 32 antennas.

In a further feature the image chamber further includes a protective ring around the entry opening to protect the human head from injury when inserting the head through the entry opening.

Broadly defined, the present invention according to another aspect is a method of using an electromagnetic tomography (EMT) system to generate a data tensor for imaging a human head, including: positioning a patient on his back on a patient support; inserting the head of the patient horizontally through a front entry opening of an image chamber unit, the image chamber unit including an antenna assembly at least partially defining a horizontally-oriented imaging chamber and including an array of antennas arranged around the imaging chamber, the array of antennas including at least some transmitting antennas and at least some receiving antennas; and using a control system, causing the transmitting antennas to transmit a low power electromagnetic field that is received by the receiving antennas after passing through the patient's head in the imaging chamber and producing a data tensor from resulting signals that may be inversed to reconstruct a 3D distribution of dielectric properties within the human head and thereby to create an image of the patient's head. The image chamber unit includes a housing that at least partially contains the antenna assembly, wherein the front entry opening is in the housing, and wherein the method further includes providing a membrane, within the imaging chamber, that separates a front portion of the imaging chamber from a rear portion.

In a feature of this aspect, the method includes a step of conforming the flexible membrane to a portion of the shape of the patient's head when the head is inserted through the front entry opening and into the front portion of the imaging chamber.

In a feature of this aspect, the method further includes a step of filling the rear portion of the imaging chamber with a liquid. The liquid is a matching liquid for an electromagnetic tomography operation. The matching liquid is a mixture of glycerol, water and brine. The antenna assembly further includes a back disk attached to a rear of a plurality of antenna disks, and wherein the method further includes pumping the matching liquid into the rear portion of the imaging chamber through at least one inlet in the back disk. In a further feature of this aspect the method further includes a step of positioning a catch basin adjacent the entry opening so as to receive liquid leaking from the front of the imaging chamber. The catch basin includes a drain tube.

In a further feature the method includes a step of placing a sanitary protective cap over the patient's head so that the protective cap is disposed between the patient's head and the flexible membrane to provide sanitary protection for a human head when the human head is inserted into the front entry opening and against the membrane.

Broadly defined, the present invention according to another aspect is a method of using an electromagnetic tomography (EMT) system to generate a data tensor for imaging a human head, including: in response to an emergency report and request from or on behalf of stroke patient, providing an ambulance equipped with an image chamber unit for gathering measurement data pertaining to a human head in an electromagnetic tomography (EMT) system, the image chamber unit including: an antenna assembly at least partially defining a horizontally-oriented imaging chamber and including an array of antennas arranged around the imaging chamber, the array of antennas including at least some transmitting antennas and at least some receiving antennas, wherein the transmitting antennas transmit a low power electromagnetic field, wherein the receiving antennas receive the low power electromagnetic field after passing through a human head in the imaging chamber and provide corresponding signals to a control system so as to produce a data tensor that may be inversed to reconstruct a 3D distribution of dielectric properties within the human head and thereby to create an image of the object, and a housing, at least partially containing the antenna assembly, having a front entry opening into the imaging chamber; positioning the stroke patient on his back on a patient support; inserting the head of the patient horizontally through the front entry opening of the image chamber unit and into the imaging chamber; using a control system, causing the transmitting antennas to transmit a low power electromagnetic field that is received by the receiving antennas after passing through the patient's head in the imaging chamber and producing a data tensor from resulting signals that may be inversed to reconstruct a 3D distribution of dielectric properties within the human head and thereby to create an image of the patient's head; providing the data tensor to a hub computer system; producing EMT image results based on the provided data; and providing the EMT image results to a medical practitioner at a treatment center for use in diagnosing or treating the stroke patient upon the patient's arrival at the treatment center.

In a feature of this aspect, the method further includes providing a membrane, within the imaging chamber, that separates a front portion of the imaging chamber from a rear portion. In a further feature of this aspect, the method further includes a step of conforming the flexible membrane to a portion of the shape of the patient's head when the head is inserted through the front entry opening and into the front portion of the imaging chamber. In a further feature of this aspect, the method further includes a step of filling the rear portion of the imaging chamber with a liquid. The liquid is a matching liquid for an electromagnetic tomography operation. The matching liquid is a mixture of glycerol, water and brine. The antenna assembly further includes a back disk attached to a rear of a plurality of antenna disks, and wherein the method further includes pumping the matching liquid into the rear portion of the imaging chamber through at least one inlet in the back disk.

In a further feature the method includes the step of positioning a catch basin adjacent the entry opening so as to receive liquid leaking from the front of the imaging chamber. The catch basin includes a drain tube.

In yet a further feature the method includes the step of placing a sanitary protective cap over the patient's head so that the protective cap is disposed between the patient's head and the flexible membrane to provide sanitary protection for a human head when the human head is inserted into the front entry opening and against the membrane Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

Further features, embodiments, and advantages of the present invention will become apparent from the following detailed description with reference to the drawings, wherein.

DETAILED DESCRIPTION

Figure 1:
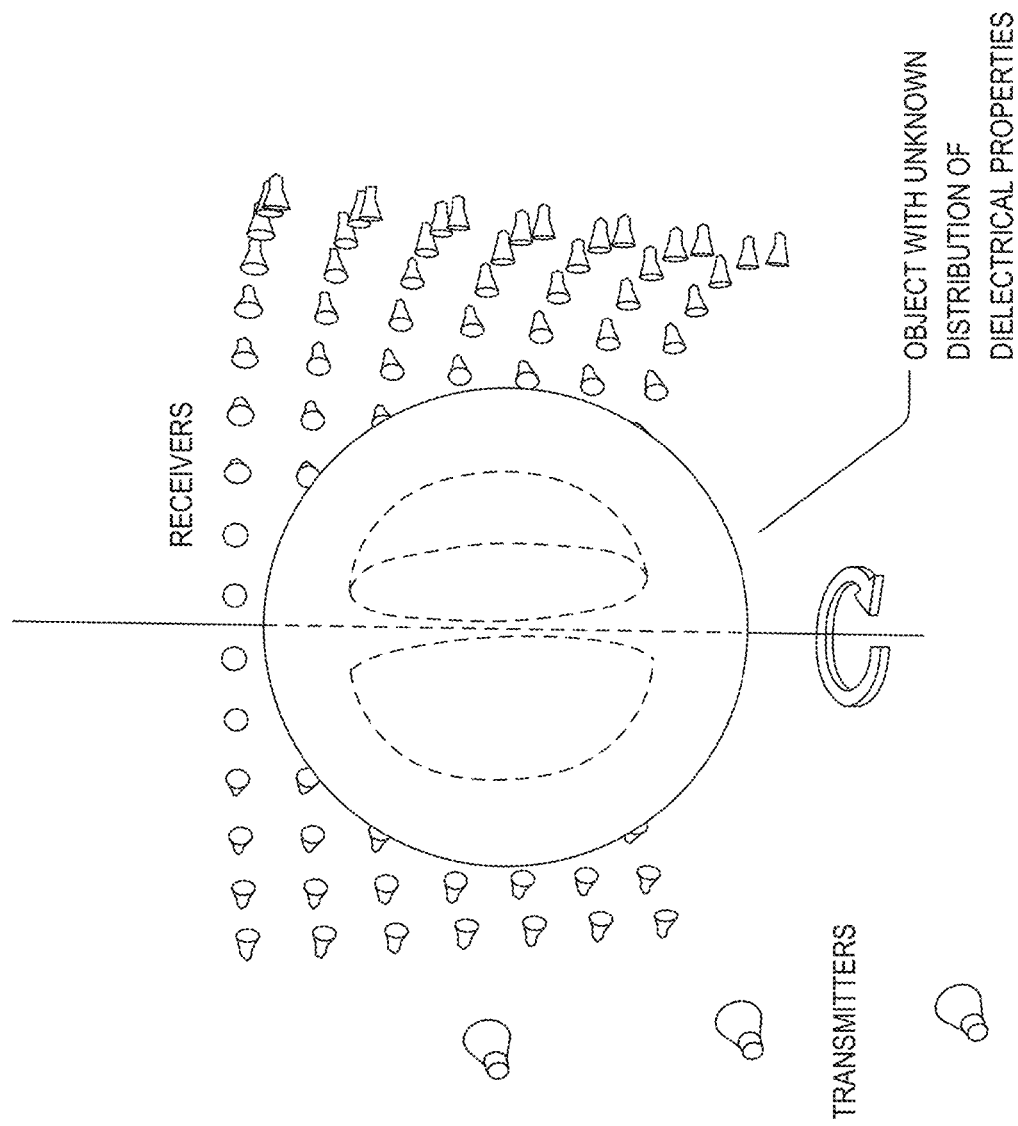
FIG. 1 is a graphical illustration of the principle of electromagnetic tomography (EMT)
Figure 2:
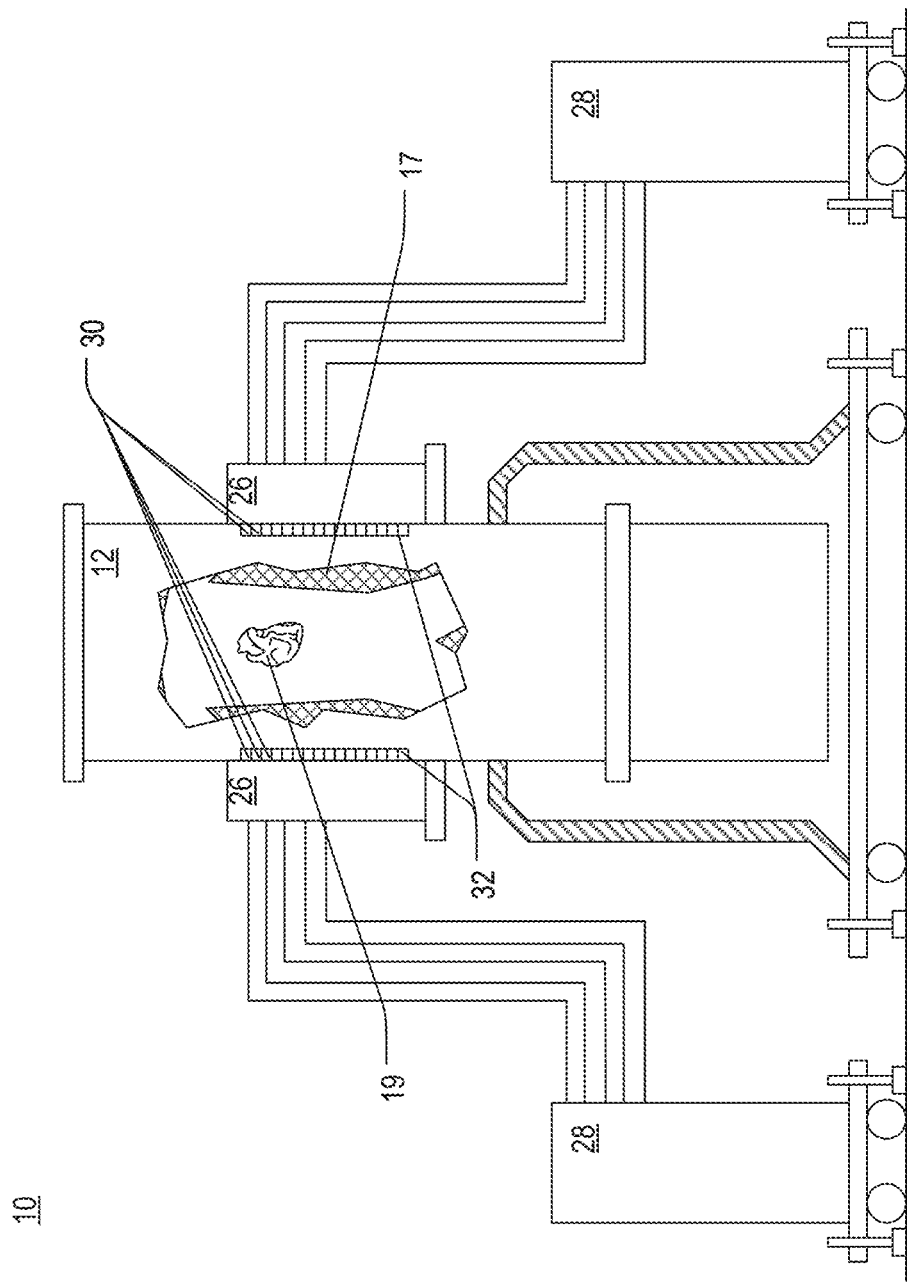
FIG. 2 is a schematic view of a prior art EM field tomographic spectroscopic system.
Figure 3:
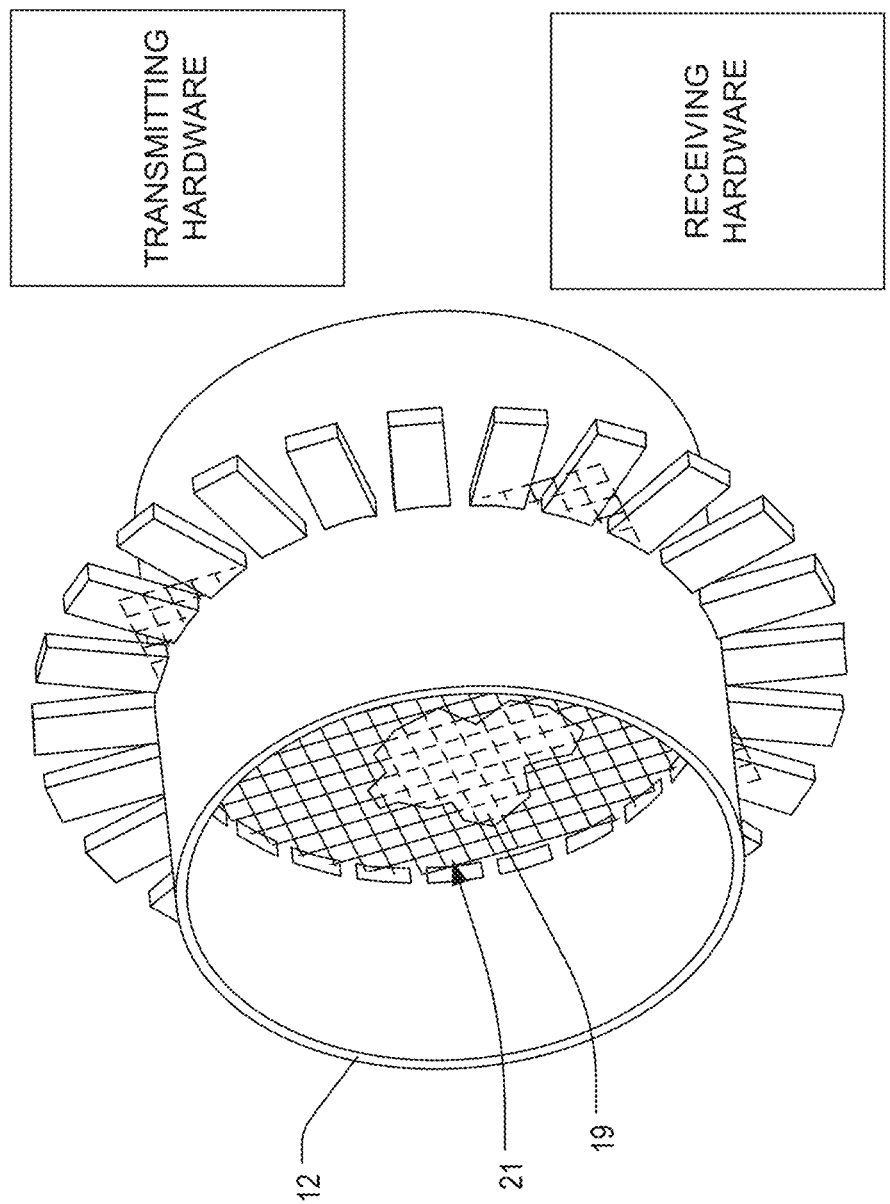
FIG. 3 is a schematic diagram illustrating the operation of the system of FIG. 1 in a two-dimensional context.
Figure 4:
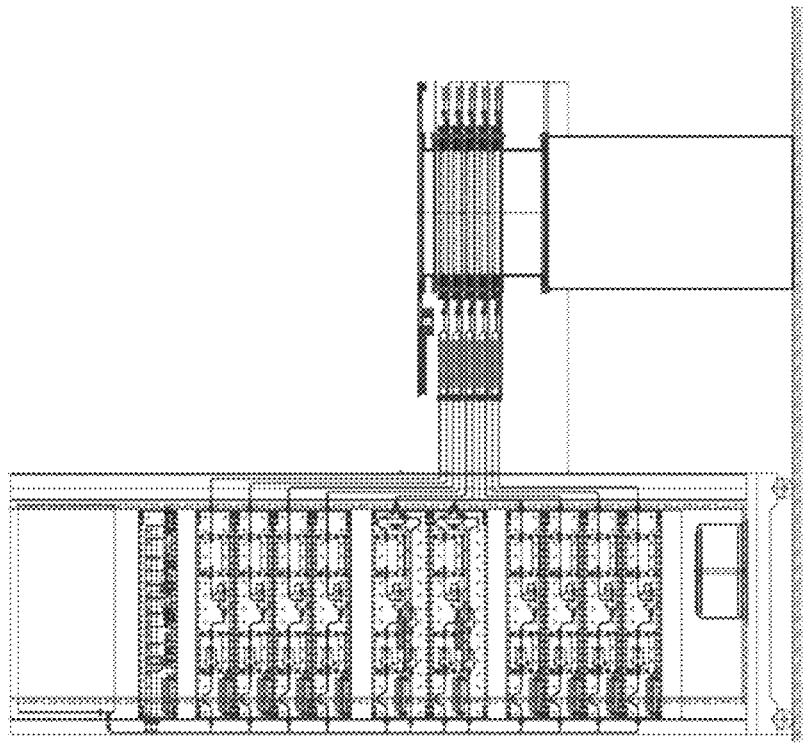
FIGS. 4 and 5 are schematic illustrations of two three-dimensional settings for the system of FIG. 2.
Figure 5:
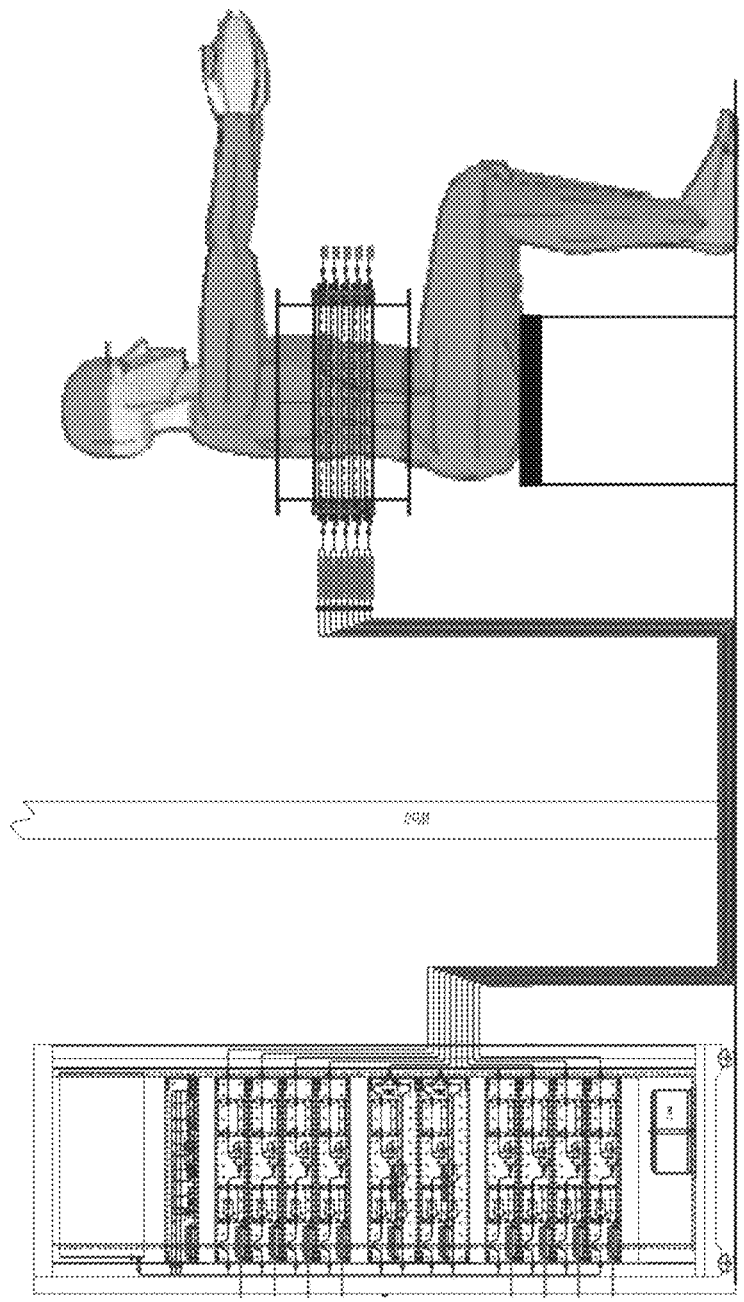

As a preliminary matter, it will readily be understood by one having ordinary skill in the relevant art ("Ordinary Artisan") that the present invention has broad utility and application. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. § 112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers," "a picnic basket having crackers without cheese," and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, in which like numerals represent like components throughout the several views, one or more preferred embodiments of the present invention are next described. The following description of one or more preferred embodiment(s) is merely exemplary in nature and is in no way intended to limit the invention, its application, or uses.

Figure 6:
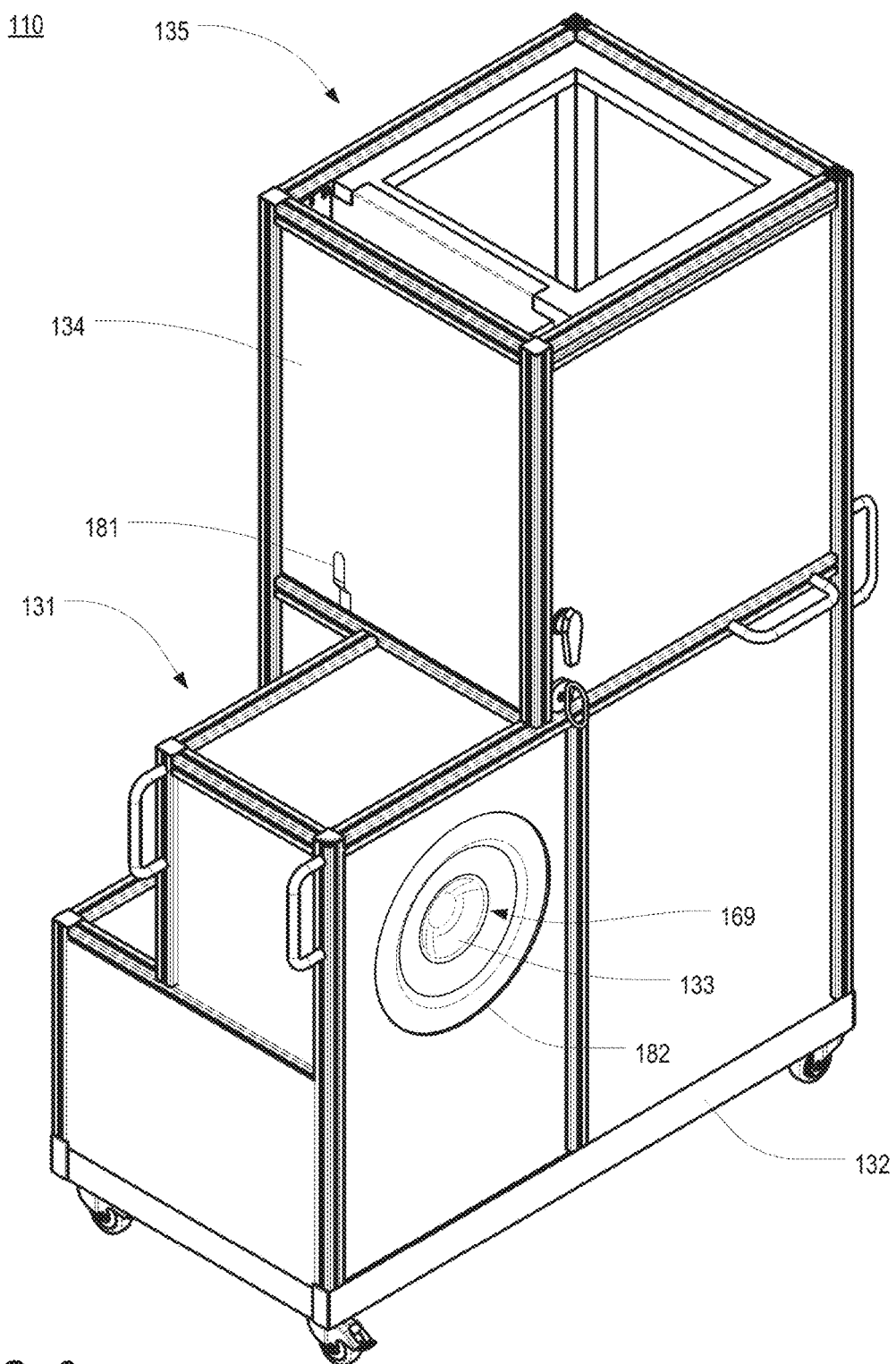
FIG. 6 is a front isometric view of an EMT system for imaging a human head in accordance with one or more preferred embodiments of the present invention.
Figure 7:
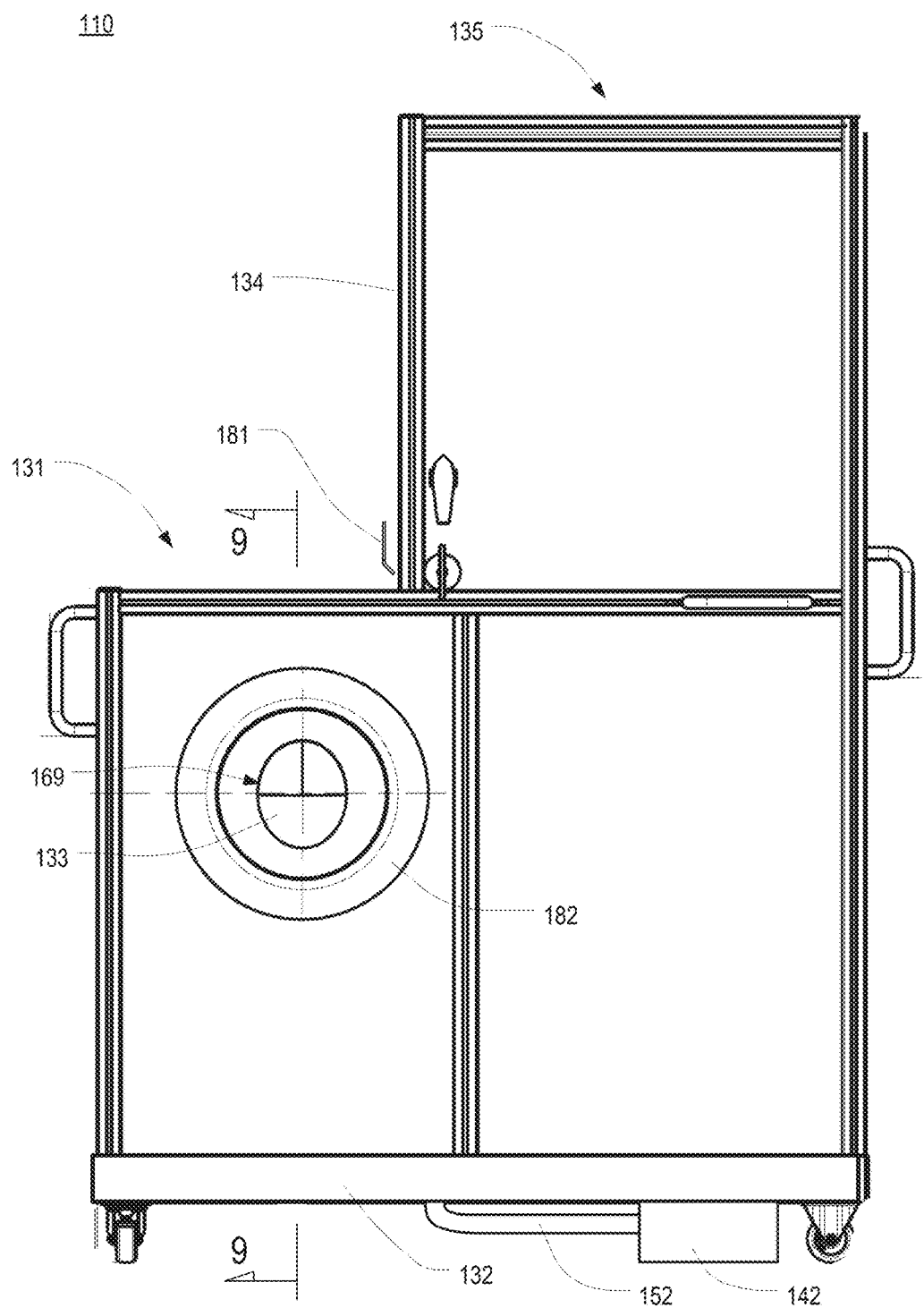
FIG. 7 is a front plan view of the EMT system of FIG. 6.
Figure 8:
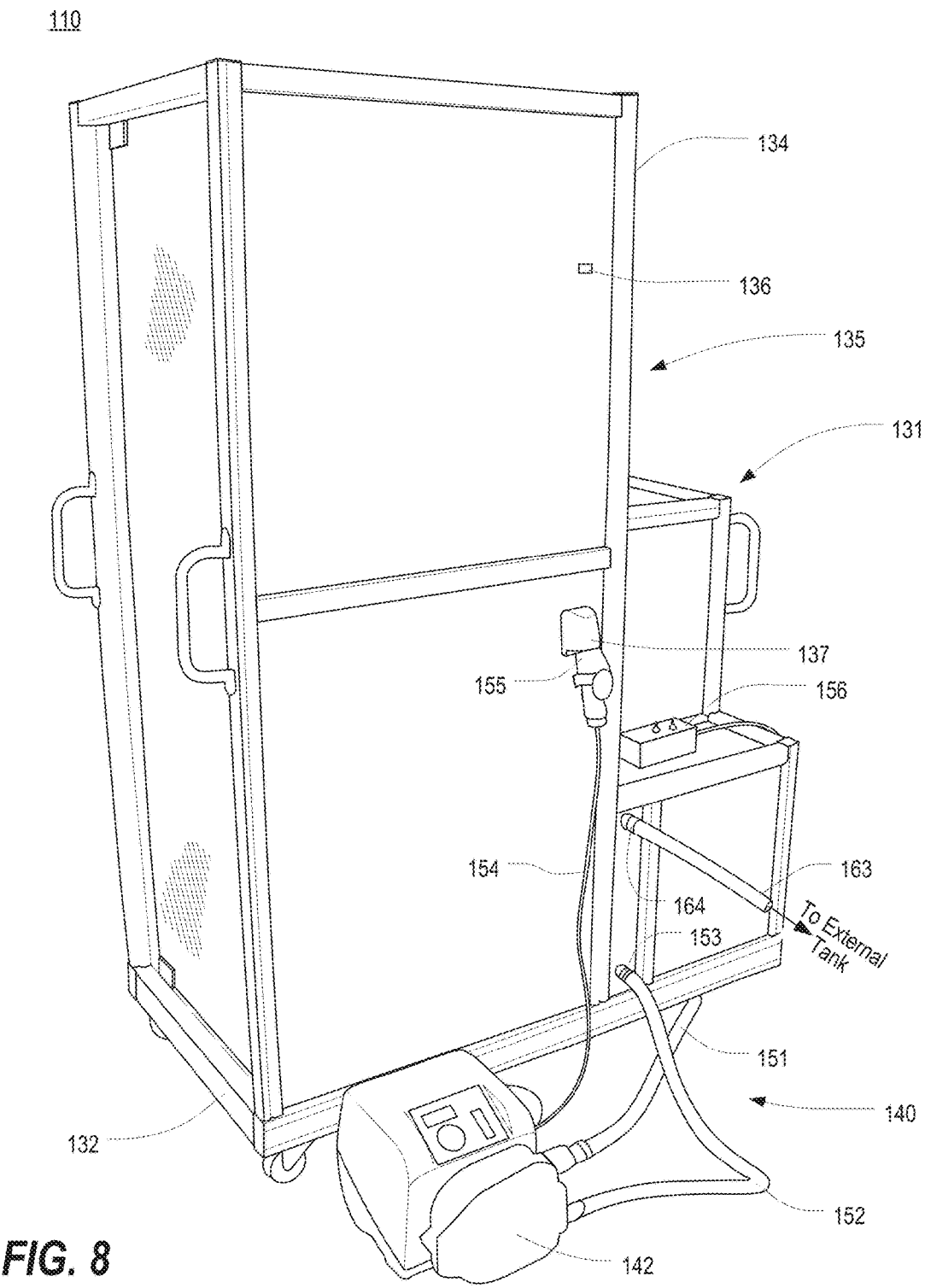
FIG. 8 is a rear perspective view of the EMT system of FIG. 6.

FIG. 6 is a front isometric view of an EMT system 110 for imaging a human head 19 in accordance with one or more preferred embodiments of the present invention, FIG. 7 is a front plan view of the EMT system 110 of FIG. 6, and FIG. 8 is a rear perspective view of the EMT system 110 of FIG. 6. As shown therein, the system 110 includes an image chamber unit 131, a control cabinet 135, a hydraulic system 140 for supplying, circulating, and otherwise managing a matching fluid to the image chamber unit 131, and a rolling carriage 132. In at least some embodiments, the image chamber unit 131 and the control cabinet 135 are housed together in a single enclosure 134 and are supported on a rolling carriage 132. Furthermore, in at least some embodiments, some or all of the hydraulic system 140 is supported on the rolling carriage 132 as well. However, in some embodiments, the image chamber unit 131 and control cabinet 135 are separate from each other and each may or may not be carried on its own rolling carriage. In some of these embodiments, the image chamber unit 131 and control cabinet 135 are not located in the same room. Although not illustrated in FIGS. 6-8, the system 110 also includes a user interface computer 208, described elsewhere herein, which may be connected to the rest of the system 110 via Ethernet or other port 136 located on the side of the control cabinet 131.

Figure 9:
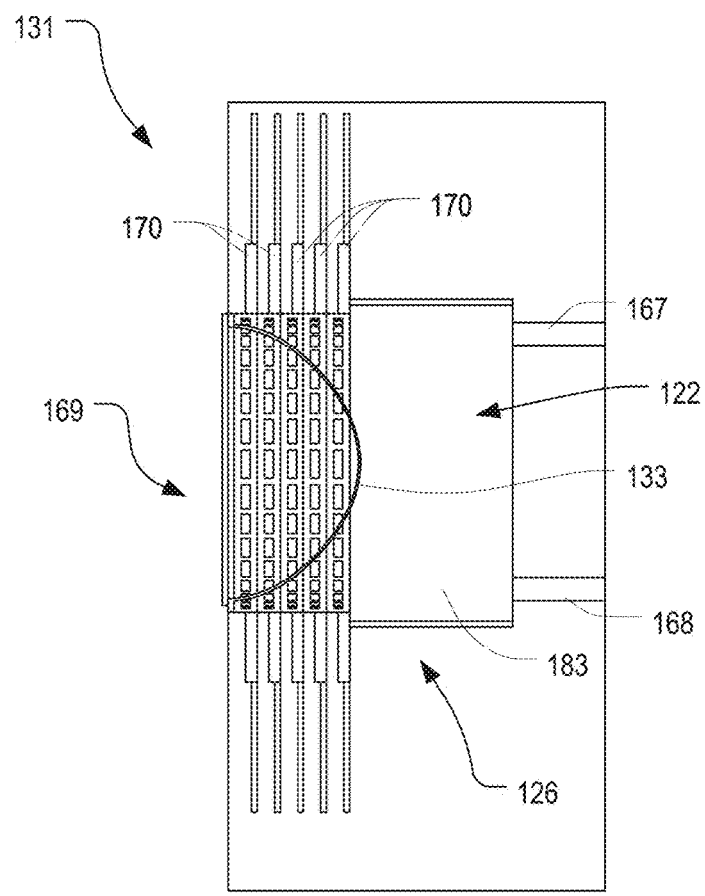
FIG. 9 is a cross-sectional, partially schematic, right side view of the image chamber unit of FIG. 7, taken along line 9-9.

FIG. 9 is a cross-sectional, partially schematic, right side view of the image chamber unit 131 of FIG. 7, taken along line 9-9. As shown therein, the image chamber unit 131 includes a disk assembly 126, a membrane 133, and fluid inlets 167,168. The disk assembly 126 includes a plurality of antenna disks 170 and a back disk 183, wherein at least the antenna disks 170 are open in their centers. The center openings of the antenna disks 170 together with the back disk 183 at least partially define a "working" chamber or "imaging" chamber 122. In at least some embodiments, the antenna disk center openings are circular, and the circular openings thus define a cylindrical portion of the working chamber 122 (perhaps best seen in FIG. 17), which simplifies the operation of the tomography somewhat, but in other embodiments the center openings and working chamber 122 may take on other shapes. In at least some embodiments, the volume of the working chamber 122 is approximately 12 liters.

Figure 10:
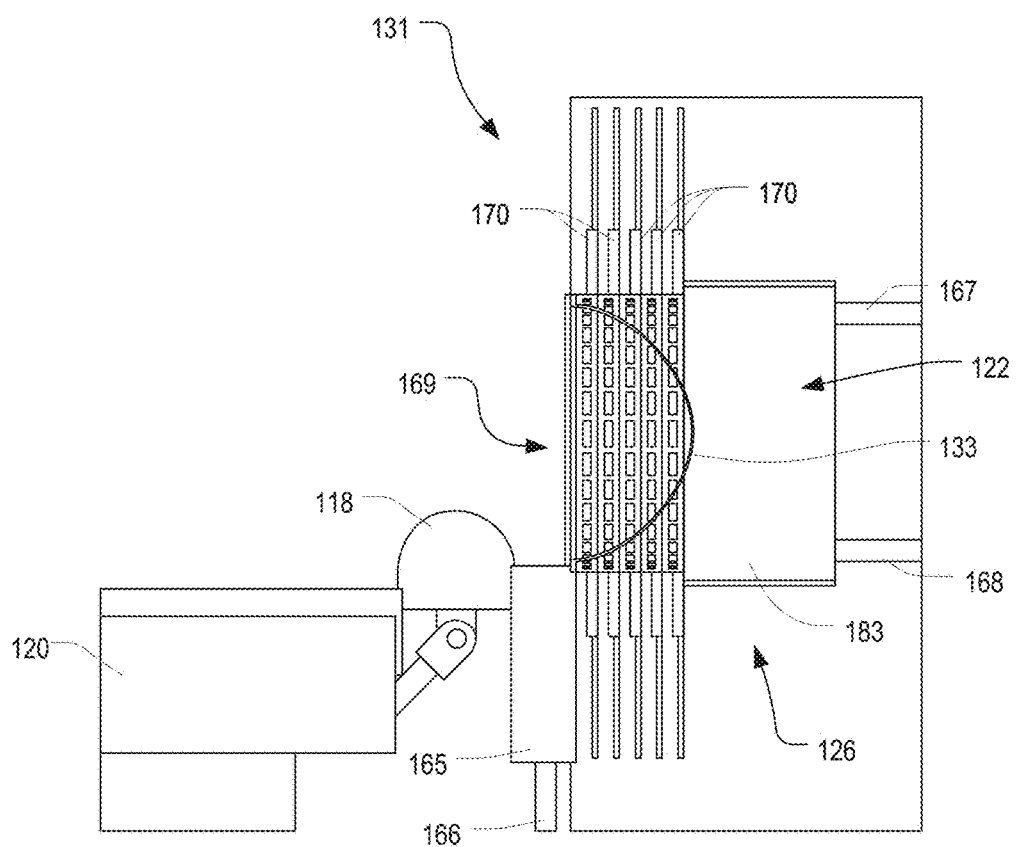
FIG. 10 is a view of the image chamber unit similar to that of FIG. 9, but shown with a patient support and a catch basin in place adjacent the unit.
Figure 11:
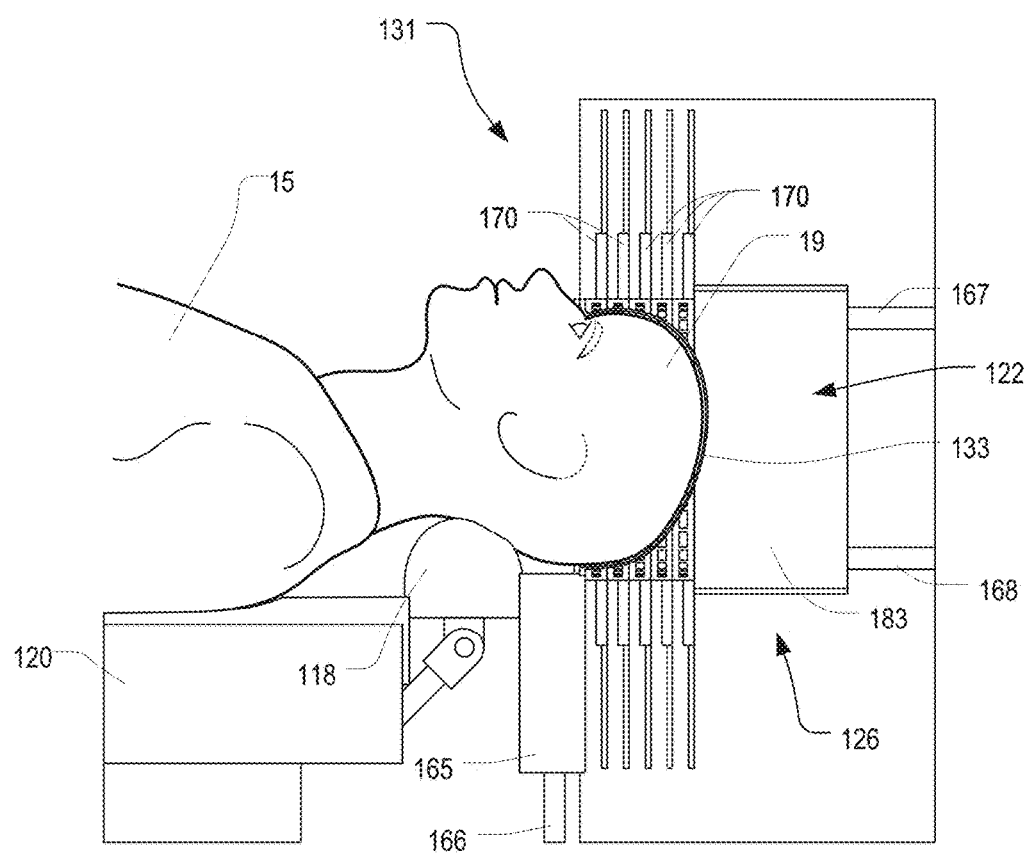
FIG. 11 is a view of the image chamber unit similar to that of FIG. 10, but shown with an upper portion of a patient's head inserted into the entry opening.

The center opening of the frontmost antenna disk 170 defines an entry opening 169 for receiving a patient. The entry opening 169 is preferably surrounded by a protective ring 182 (shown in FIGS. 6 and 7) covering the surfaces of the antenna disk 170 and other portions of the working chamber 122. FIG. 10 is a view of the image chamber unit 131 similar to that of FIG. 9, but with a patient support 120 and a catch basin 165 in place adjacent the unit 131, and FIG. 11 is a view of the image chamber unit 131 similar to that of FIG. 10 but shown with an upper portion of a patient's head 19 inserted into the entry opening. For comfort and convenience, the patient may be positioned on the patient support 120, which may be a gurney, cart, table, stretcher, or the like. In at least some embodiments of the present invention, a headrest 118 extends from the end of the patient support 120. The headrest 118 is preferably padded and adjustable. Adjustability of the headrest 118 may be provided in one or more of the longitudinal direction (toward or away from the end of the patient support 120), the vertical direction (up or down relative to the patient support 120), and rotationally (for example, about an axis that is parallel with the end of the patient support 120). In the illustrated embodiment, the entry opening and the working chamber 122 are sized to correspond specifically to a human head, but it will be appreciated that other dimensions may be utilized for other body parts or to accommodate the entirety of a human body. The entry opening is substantially liquid-sealed by the membrane 133 such that the front of the working chamber 122 is separated by the membrane 133 from the rear of the chamber 122. Fluid leaks through the front of the working chamber 122, such as around or through the membrane 133, may be captured in the catch basin 165 disposed in front of the unit 131. It is contemplated that the catch basin 165 can be integral with or otherwise part of the image chamber unit 131.

Figure 12:
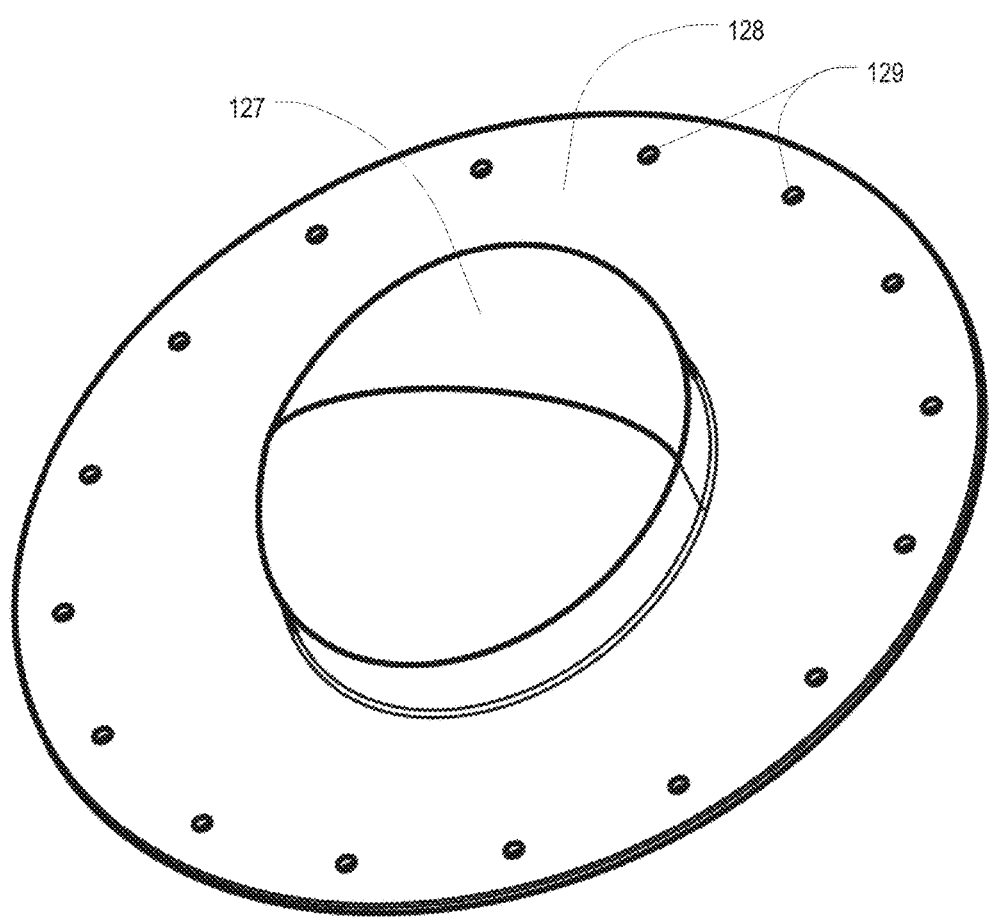
FIGS. 12 and 13 are a rear isometric view and a rear plan view, respectively, of the membrane of the image chamber unit of FIG. 6.
Figure 13:
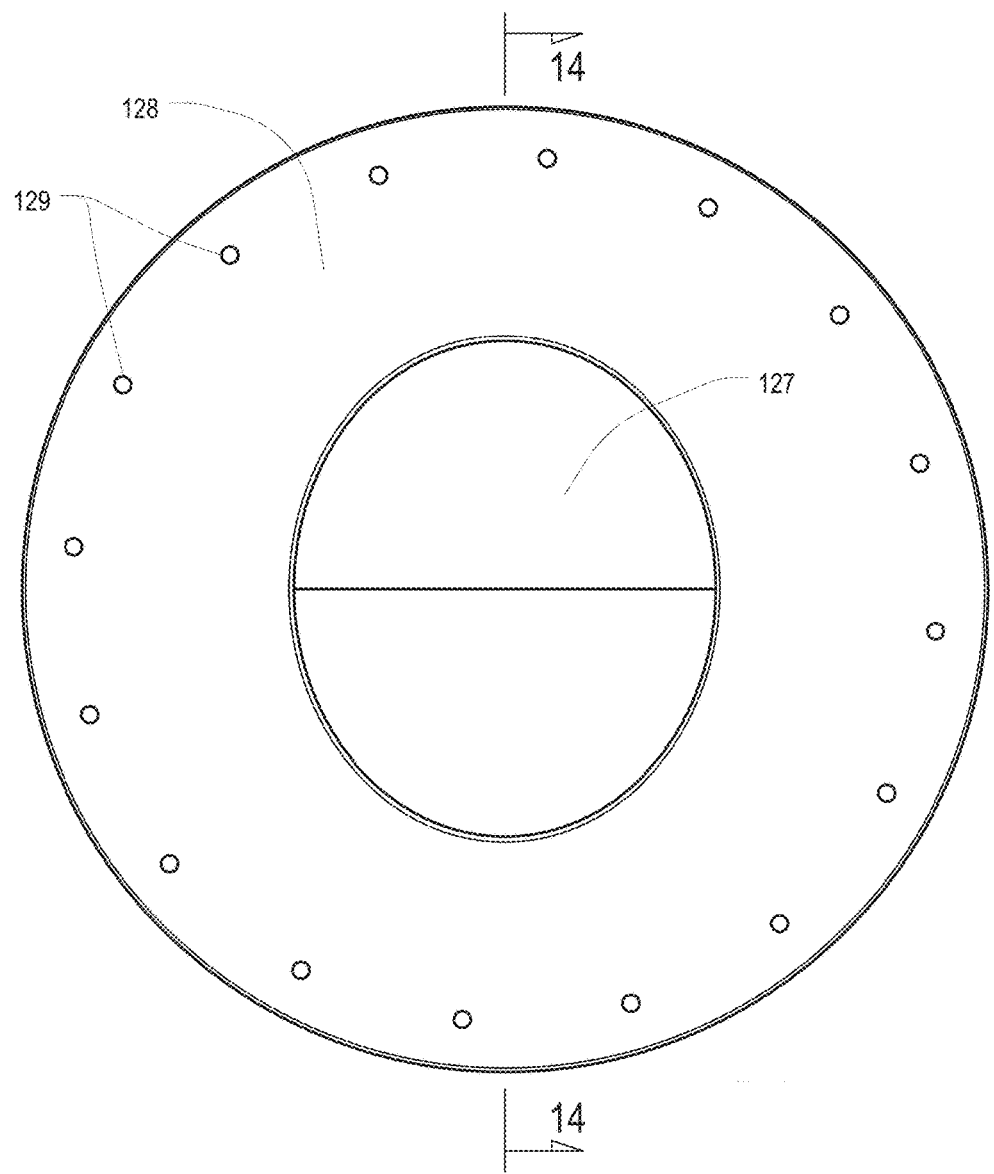
Figure 14:
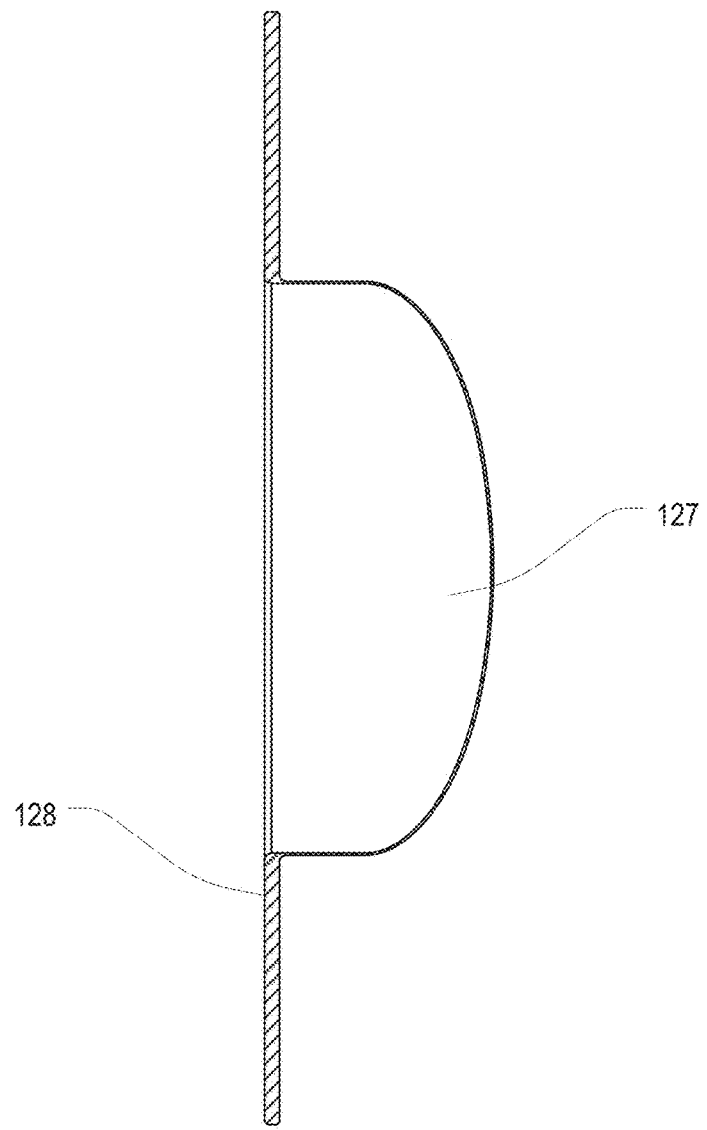
FIG. 14 is a side cross-sectional view of the membrane of FIG. 13, taken along line 14-14.

FIGS. 12 and 13 are a rear isometric view and a rear plan view, respectively, of the membrane 133 of the image chamber unit 131 of FIG. 6, and FIG. 14 is a side cross-sectional view of the membrane 133 of FIG. 13, taken along line 14-14. The membrane 133 is preferably somewhat hat-shaped, with a center crown portion 127 extending "upward" or "inward" from an outer brim portion 128. The brim portion 128 is shaped to be fastened to the antenna disks 170 and may include apertures 129 for this purpose. As shown in FIG. 14, the crown portion 127 may be thinner than the brim portion 128 and is preferably flexible enough to wrap snugly around the patient's head 19, as shown in FIG. 11. In at least some embodiments, the membrane 133 is made of latex or similar material.

Figure 15:
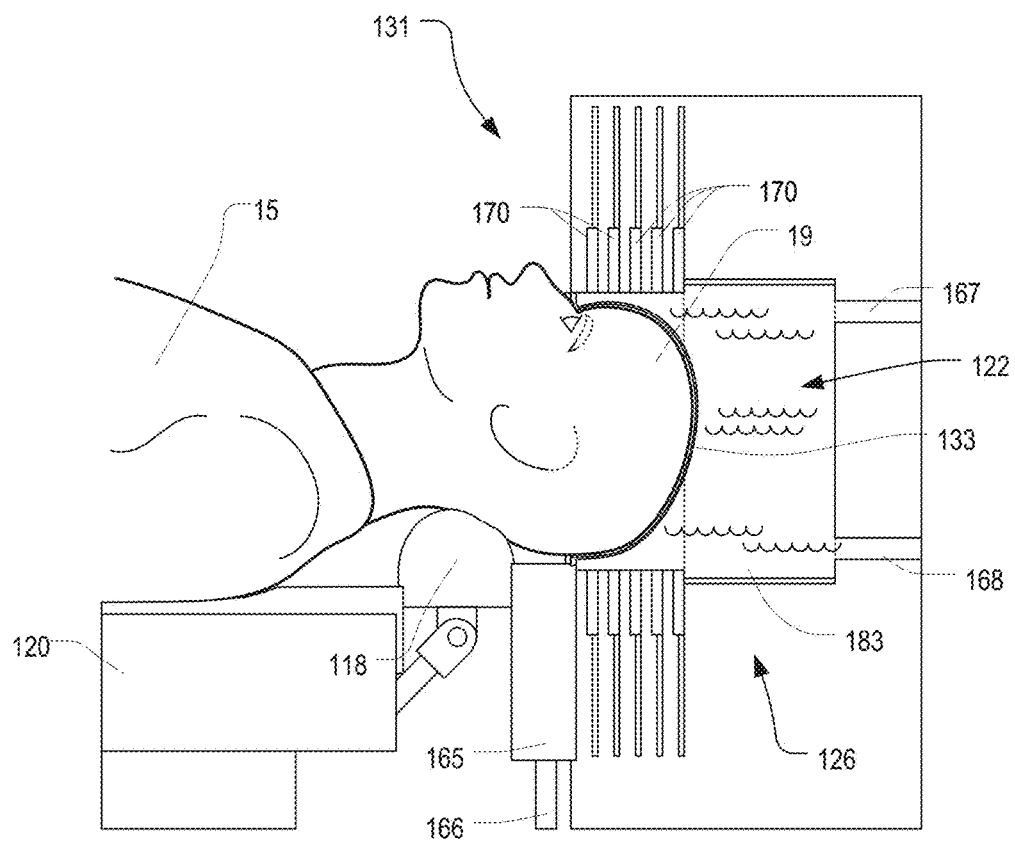
FIG. 15 is a view of the image chamber unit similar to that of FIG. 11, but shown with a fluid disposed within the working chamber on the opposite side of the membrane from the patient's head.

FIG. 15 is a view of the image chamber unit 131 similar to that of FIG. 11 but shown with a fluid disposed within the working chamber 122 on the opposite side of the membrane 133 from the patient's head 19. The fluid may be supplied to or from the working chamber 122 via the inlets 167,168, which may be arranged in or on the back disk 183. The fluid itself is a "matching" fluid that is chosen for its properties so as to enhance the tomographic process. Flow and other movement of the fluid is controlled by the hydraulic system 140.

Figure 16:
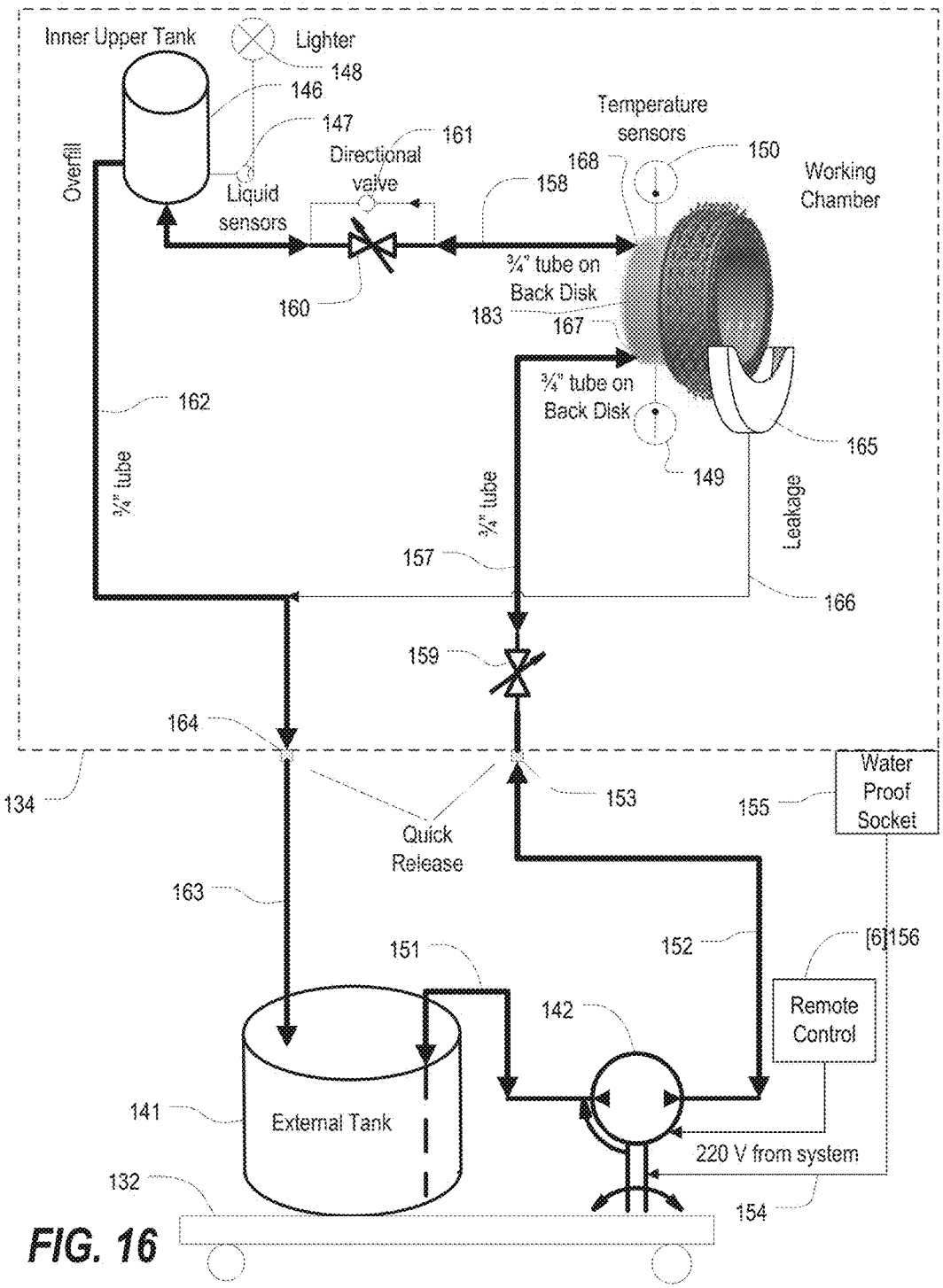
FIG. 16 is a schematic diagram of the hydraulic system of FIG. 8.

FIG. 16 is a schematic diagram of the hydraulic system 140 of FIG. 8. As shown therein, the hydraulic system 140 includes an external tank 141, a bi-directional pump 142, a valve 159, backflow valve 160, a check (directional) valve 161, an inner upper tank 146, one or more liquid sensors 147, a lighter 148, one or more temperature sensors 149,150, and a variety of hoses, tubes, fittings, and the like, some of which are described herein. The external tank 141 holds a quantity of a matching fluid. A hose 151 connects the external tank 141 to the pump 142, and another hose 152 connects the pump 142 to a fitting 153 on the enclosure 134. In at least some embodiments, the pump hoses 151,152 are ¾" flexible tube hoses, and the hose fitting 153 is a quick release fitting.

The pump 142 is used to supply matching fluid from the external tank 141 to the working (image) chamber of the image chamber unit 131. The matching fluid is a solution or gel that is needed or useful inside the imaging chamber when the object 19 is being measured inside it to address electromagnetic body-matching problems. In at least some embodiments, the matching liquid is a mixture of glycerol (Ph. Eur.), water and brine. In at least some embodiments, the pump 142 is connected by cable 154 to a standard power supply, such as a 220V electrical source, which may be provided from the control cabinet 135 via an outlet 137, preferably located on the outer surface of the enclosure 134, and a corresponding water proof socket 155. Direction, speed, and other control of the pump 142 may be provided by remote control 156. One pump 142 suitable for use in at least some preferred embodiments is a Watson Marlow 620 RE IP66 pump.

Inside the image chamber unit 131, another hose 157 is connected between the external fitting 153 and a first inlet 167 to the working chamber, and still another hose 158 is connected between a second inlet 168 to the working chamber and the inner upper tank 146. In at least some embodiments, the hose 157 is a ¾" flexible tube hose. An inline valve 159 may optionally be provided in the hose 157 from the pump 134, while a backflow valve 160 and check (directional) valve 161 may be provided in the hose 158 to the inner upper tank 146. The backflow valve 160 provides at least two functions. First, when it is closed, the pump 142 may be used to generate an under-pressure, thereby denting in the membrane 133 (as seen from outside the image chamber unit 131) and readying the unit 131 for a patient's head to be inserted therein. Second, when the patient's head is positioned inside the membrane 133, opening the backflow valve 160 allows the matching fluid to flow from the reservoir 146 back to the imaging chamber, which in turn causes the patient's head to be slowly enclosed by the membrane 133 and the liquid. The check valve 161, on the other hand, performs a safety function by avoiding the buildup of an overpressure if the backflow valve 160 is closed. The check valve 161 includes a manual control lever 181, as shown in FIG. 6.

The temperature sensors 149,150 may be used to determine the temperature of the matching fluid inside the working chamber, or in close proximity thereto. If the temperature becomes uncomfortably cool, the lamp or lighter 148 may be utilized to trigger heating of the inner upper tank 146. Unintentional heating of an empty tank 146 may be avoided by using the liquid sensors 147 to verify that sufficient liquid is present in the tank.

An overfill path may be provided between the inner upper tank 146 and the external tank 141 so as to return any excess matching liquid to the external tank 141. The overfill path may include an internal hose 162, an external hose 163, and a fitting 164 on the exterior of the enclosure 134, wherein the internal hose 162 is connected between the inner upper tank 146 and the fitting 164 and the external hose is connected between the fitting 164 and the external tank 141. Generally, the overfill path is only utilized if the reservoir 146 is accidentally overfilled, in which case the overfill path allows the excess liquid to return to the external tank 141. In at least some embodiments, the overfill path hoses 162,163 are ¾" flexible tube hoses, and the hose fitting 164 is a quick release fitting.

A leakage path may also be provided. The leakage path may include a catch basin 165 and a drain hose or tube 166. The catch basin 165 may be disposed adjacent the working chamber so as to receive fluid escaping therefrom, such as during dismantling of the system 110. In some embodiments, the drain hose 166 connects the catch basin 165 to the external tank, such as by the overflow path, while in others the drain hose 166 is routed to a waste tank (not shown) and/or is left open or unconnected.

Figure 17:
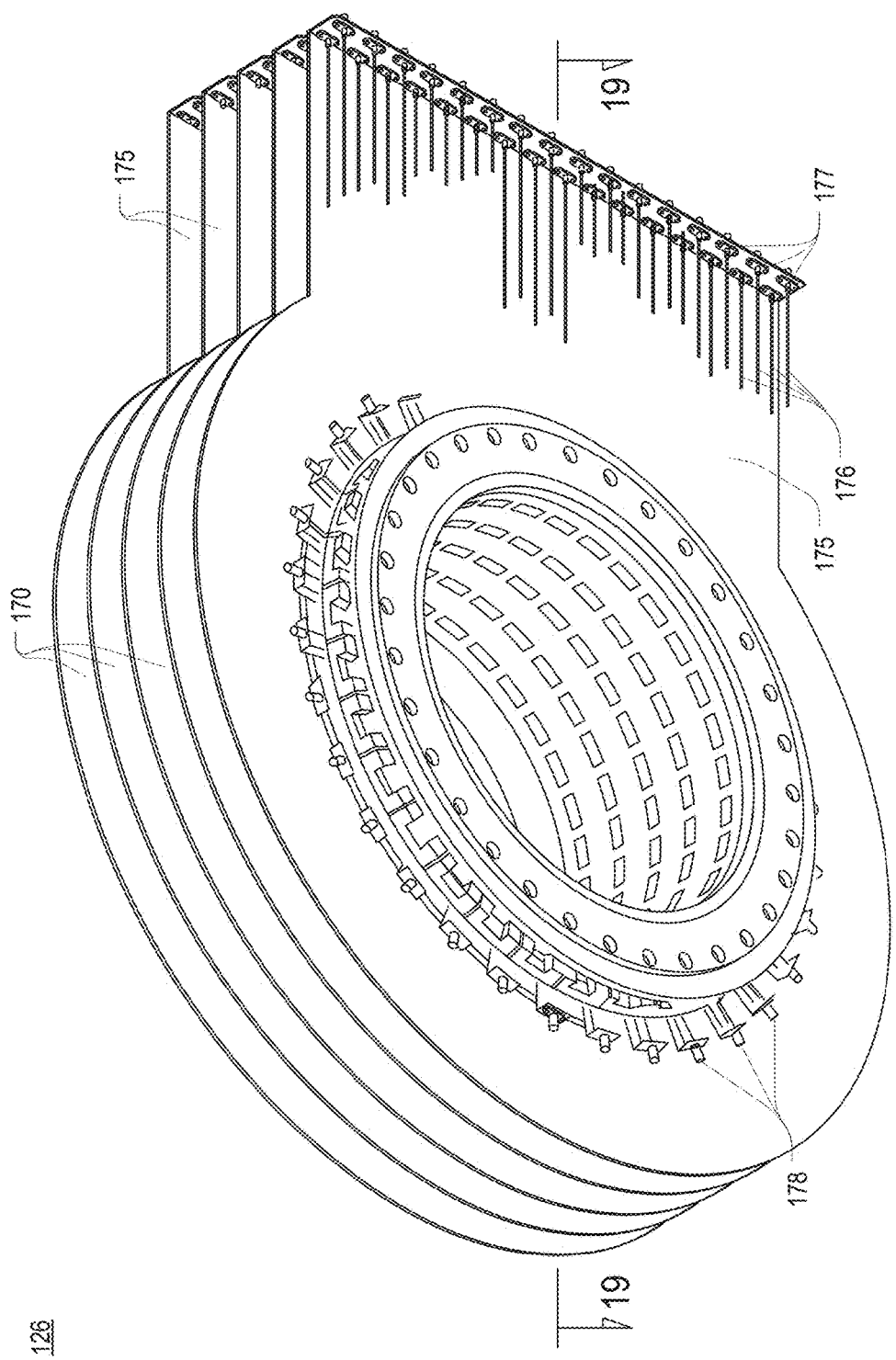
FIG. 17 is a left front isometric view of portions of the disk assembly of FIG. 9.
Figure 18:
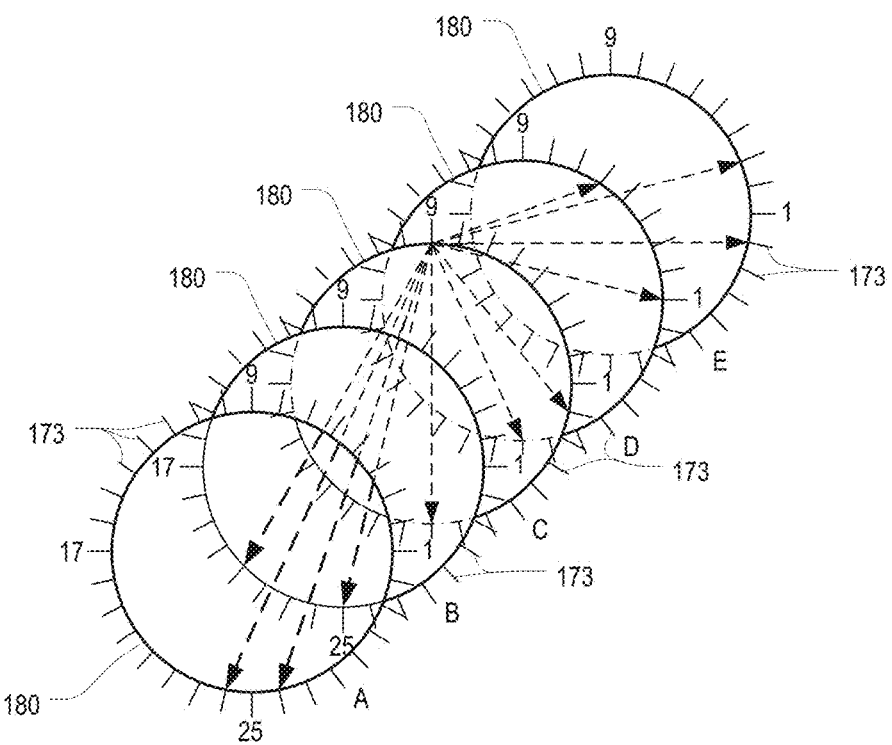
FIG. 18 is a schematic representation of concentric rings of antennas.

FIG. 17 is a left front isometric view of portions of the disk assembly 126 of FIG. 9. As shown therein, the disk assembly 126 includes a plurality of antenna disks 170 arranged concentrically such that their center openings define the interior of the working chamber 122, as described previously. Notably, whereas traditional EMT systems have used rings of transmitters/receivers/sensors that have been oriented in a horizontal plane to define a vertical working chamber, the rings of transmitter/receivers and receivers of the present invention are each oriented vertically so as to define a horizontal working chamber. Each antenna disk 170 includes a multitude of antennas 173 arranged in a ring around the working chamber 122. FIG. 18 is a schematic representation of these concentric rings 180 of antennas 173. Although other numbers of disks 170 and rings 180 may be utilized, five antenna disks 170 and thus five antenna rings 180 are present in the embodiment shown in FIGS. 17 and 18. Furthermore, although other numbers of antennas 173 may be utilized, 32 antennas 173 are present in the embodiment shown in FIGS. 17 and 18, and thus a total of 160 antennas 173 are utilized. In one embodiment, preferred for its simplicity, the antennas 173 in the middle ring 180 are both transmitting and receiving antennas, while the antennas 173 on the other four rings 180 are receiving antennas only. In one contemplated embodiment, the rings 180 (i.e., the center openings of the antenna disks 170) are 285 mm in diameter. In FIG. 17, transmitting/receiving antenna "9" on ring "C" is shown as transmitting an electromagnetic field or signal, all or some of which is received at each of various transmitting/receiving antennas on ring "C" and at each of various receiving antennas on rings "A", "B", "D", and "E". It will be appreciated, however, that any or all of the transmitting/receiving antennas on ring "C" and/or any or all of the receiving antennas on any or all of the other rings may receive the transmitted field or signal and thus may be incorporated into the tomographic process.

Figure 19:
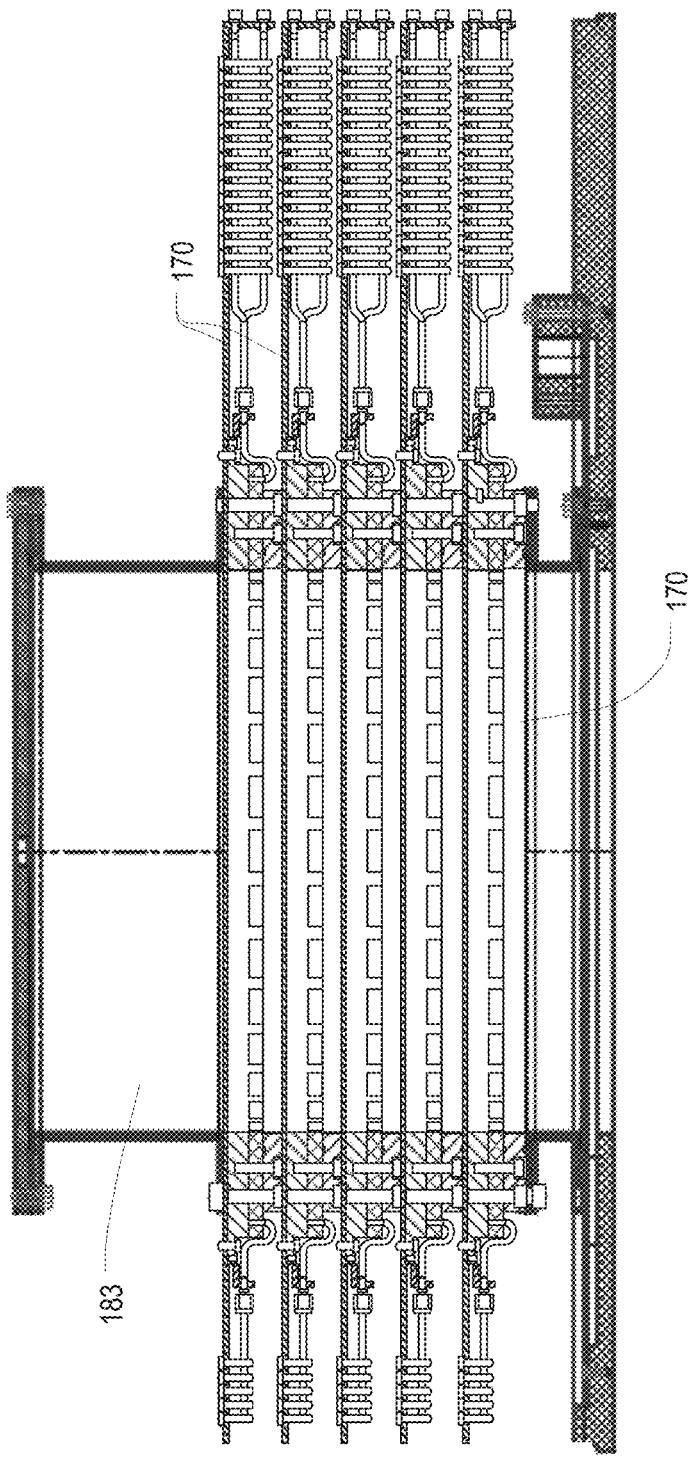
FIG. 19 is a top cross-sectional view of the disk assembly of FIG. 17, taken along line 19-19.
Figure 20:
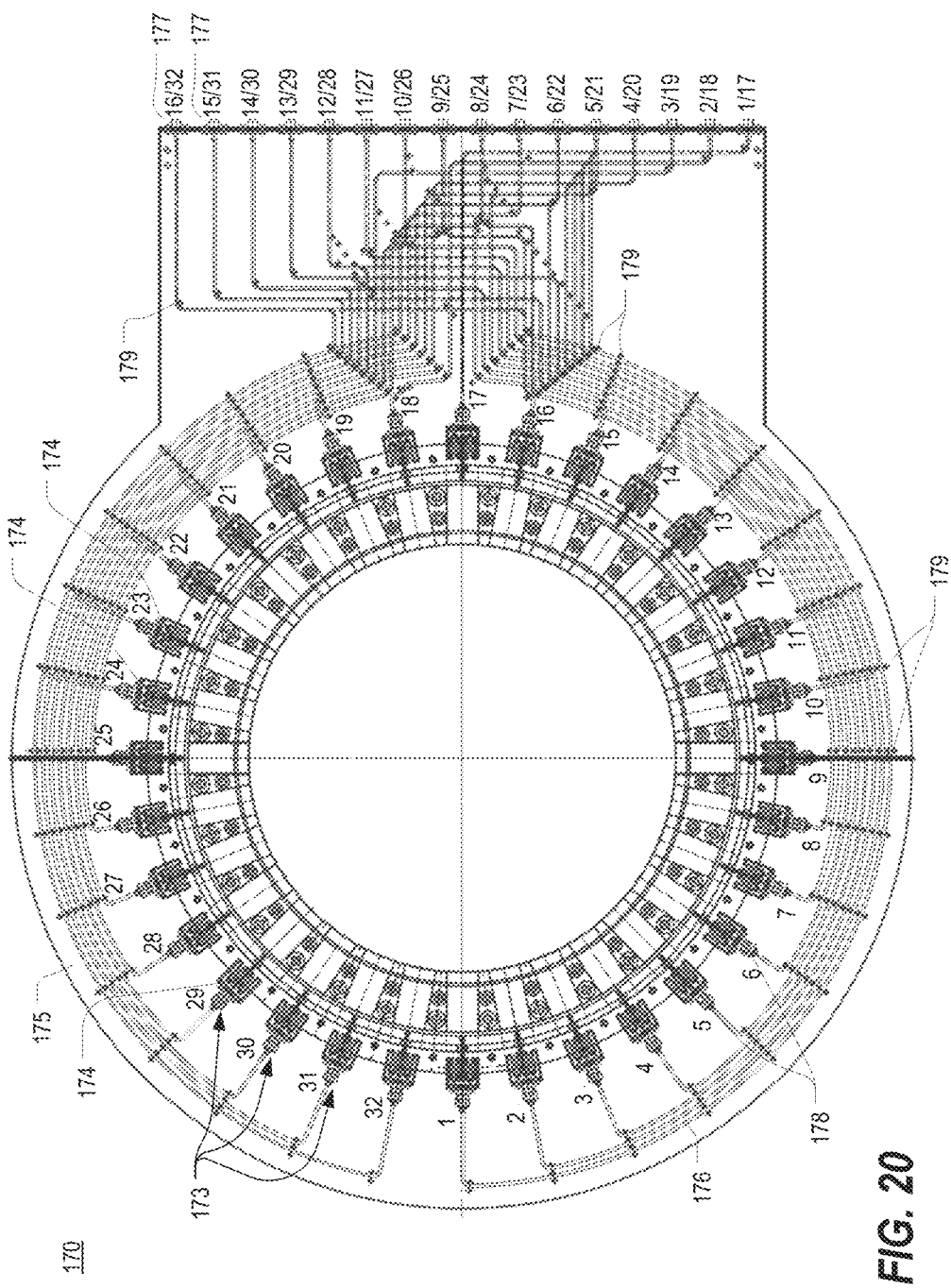
FIG. 20 is a front view of one of the antenna disks of FIG. 19.
Figure 21:
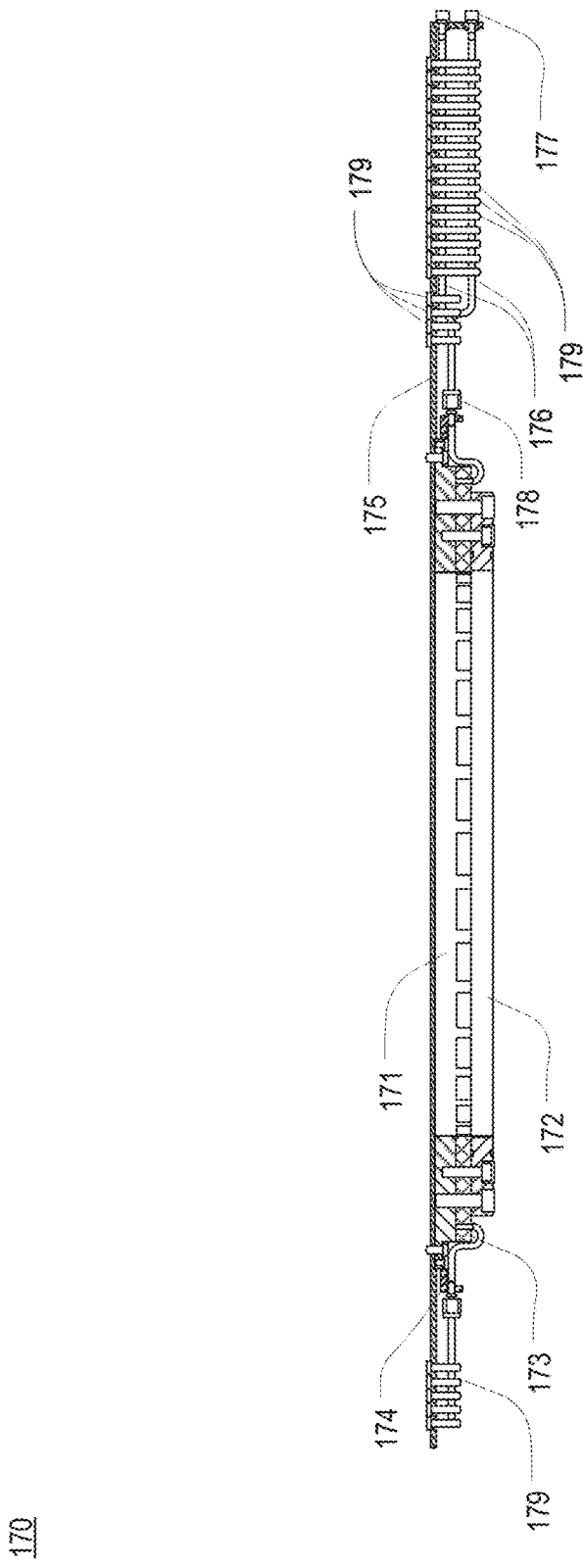
FIG. 21 is a top cross-sectional view of the antenna disk of FIG. 20.

FIG. 19 is a top cross-sectional view of the disk assembly 126 of FIG. 17, taken along line 19-19; FIG. 20 is a front view of one of the antenna disks 170 of FIG. 19, and FIG. 21 is a top cross-sectional view of the antenna disk 170 of FIG. 20. Notably, some visual detail regarding the electrical connections for the antennas has been omitted in FIG. 17; however, much of the omitted visual detail is shown in FIG. 20. Each antenna disk 170 includes two mating rings 171, 172, the antennas 173 themselves, a corner element 174 for each antenna 173, a cable plate 175, and a cable assembly 176 for each antenna 173. Each cable assembly 176 includes a cable and/or conduit with an appropriate terminator 177, 178 on each end. Screws or other cable positioners 179 are provided to hold the cable assemblies 176 in place.

Figure 22:
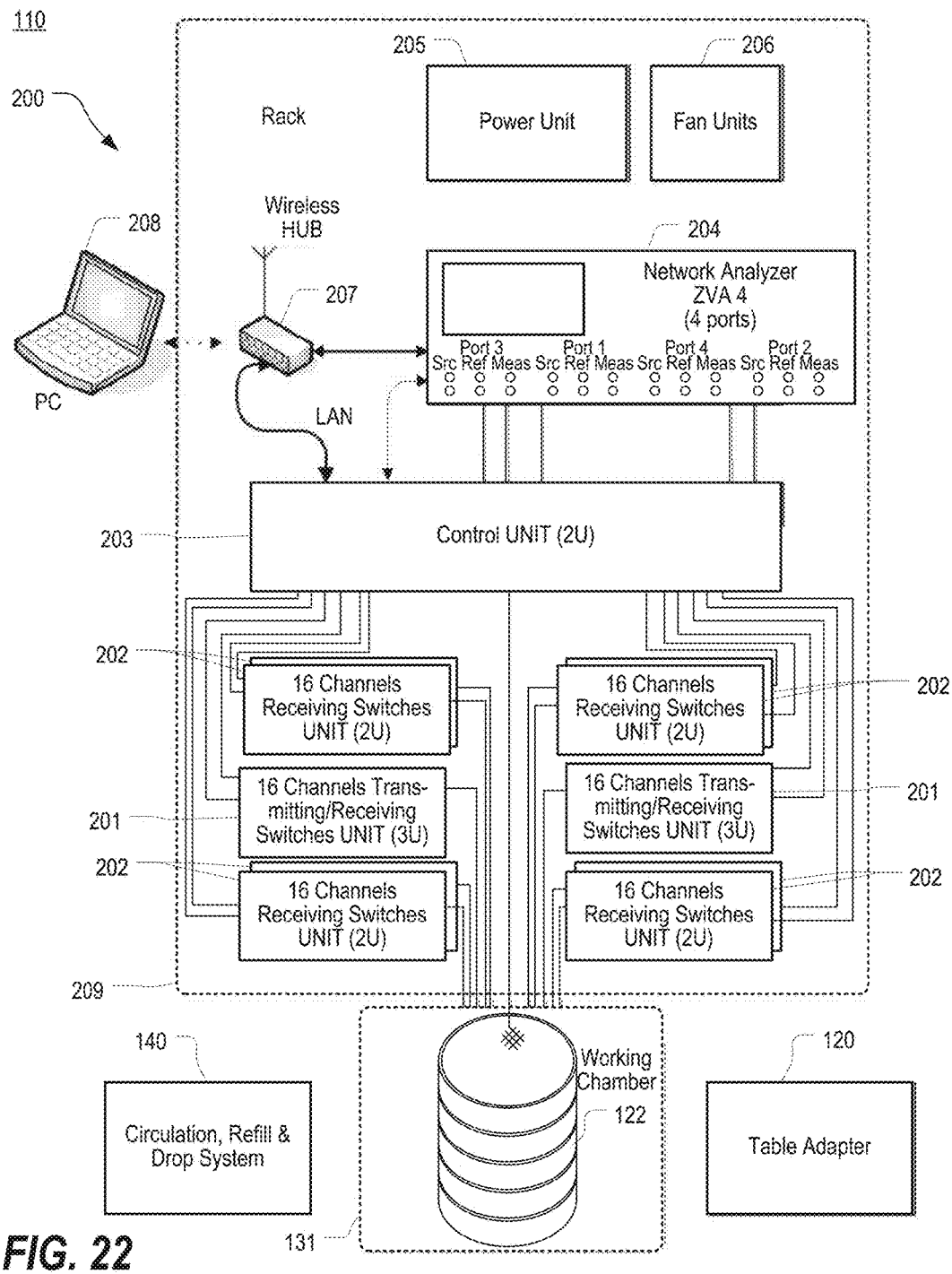
FIG. 22 is a schematic diagram of the EMT system of FIG. 6.

FIG. 22 is a schematic diagram of the EMT system 110 of FIG. 6. As shown therein, the EMT system 110 includes the image chamber unit 131 (including the working chamber 122), the hydraulic system 140, the patient support 120, and a control system 200. The control system 200 includes two 16-channel transmitting/receiving switch units 201 for the transmitting/receiving antenna disk 170, two 16-channel receiving switch units 202 for each of the receiving antenna disks 170, a control unit 203, a network analyzer 204, a power unit 205, one or more fan units 206, a hub 207, and a user interface computer 208. In at least some embodiments, the switch units 201,202, control unit 203, network analyzer 204, power unit 205, fan units 206, and hub 207 are supported on a rack 209 in the control cabinet 135. The user interface computer 208 may be supported on or in the enclosure 134 or may be supported elsewhere, such as on a nearby desk, a user's lap, or in some cases even outside the room.

Figure 23:
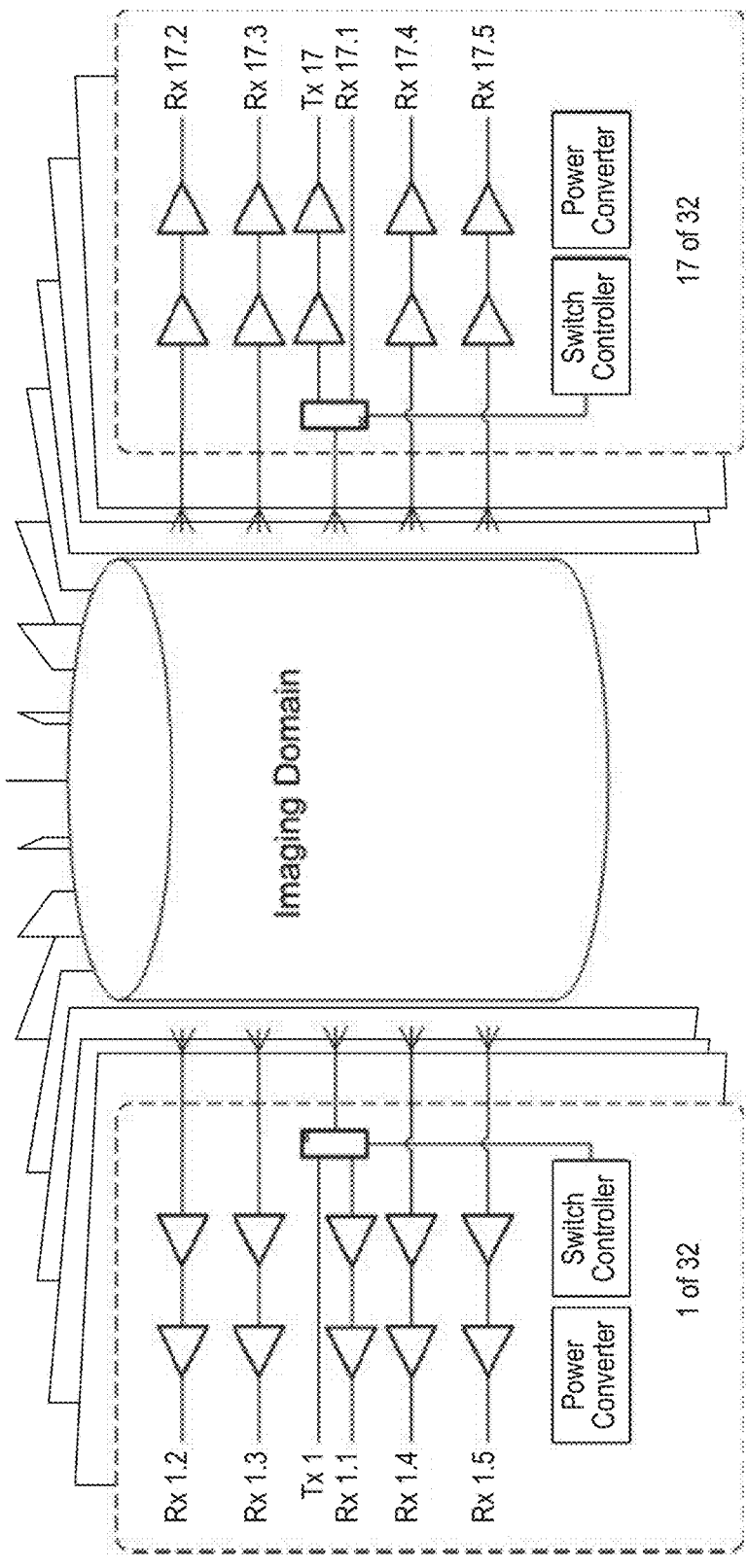
FIG. 23 is a schematic representation of the operation of the rings of antennas around the imaging domain.

FIG. 23 is a schematic representation of the operation of the rings 180 of antennas 173 around the imaging domain, which is defined by the imaging chamber. The general task is to make complex $S_{i,j,k}$ parameters matrix measurement, where i is the transmitting antenna (i=1 . . . 32), j is the receiving antenna (j=1 . . . 31), and k is the ring of the receiving antenna (k=1 . . . 5). The more practical case for the number of receiving antennas that are measured for each transmitting antenna may be between 12 and 20 (i.e., only receivers generally opposite the transmitting antenna), and the most practical case may be for 17 receiving antennas to be measured for each transmitting antenna, but other numbers are also viable. Typical attenuations may be ~90 dB to ~130 dB. In at least some embodiments, frequencies may be 0.8-1.5 GHz, step 50 MHz. In at least some embodiments, channel-to-channel isolation may be ~80 dB to ~100 dB. In at least some embodiments, maximum power output may be +20 dBm (100 mW). In at least some embodiments, single frame data acquisition time may be less than 60 mSec ("frame" being defined as the full cycle of S matrix measurements). In at least some embodiments, the number of acquired frames may be from 1 to 1000. In at least some embodiments, the dielectric properties of the matching media between antennas and object may be ~(30-to-60)+j (15-to-25).

Figure 24A:
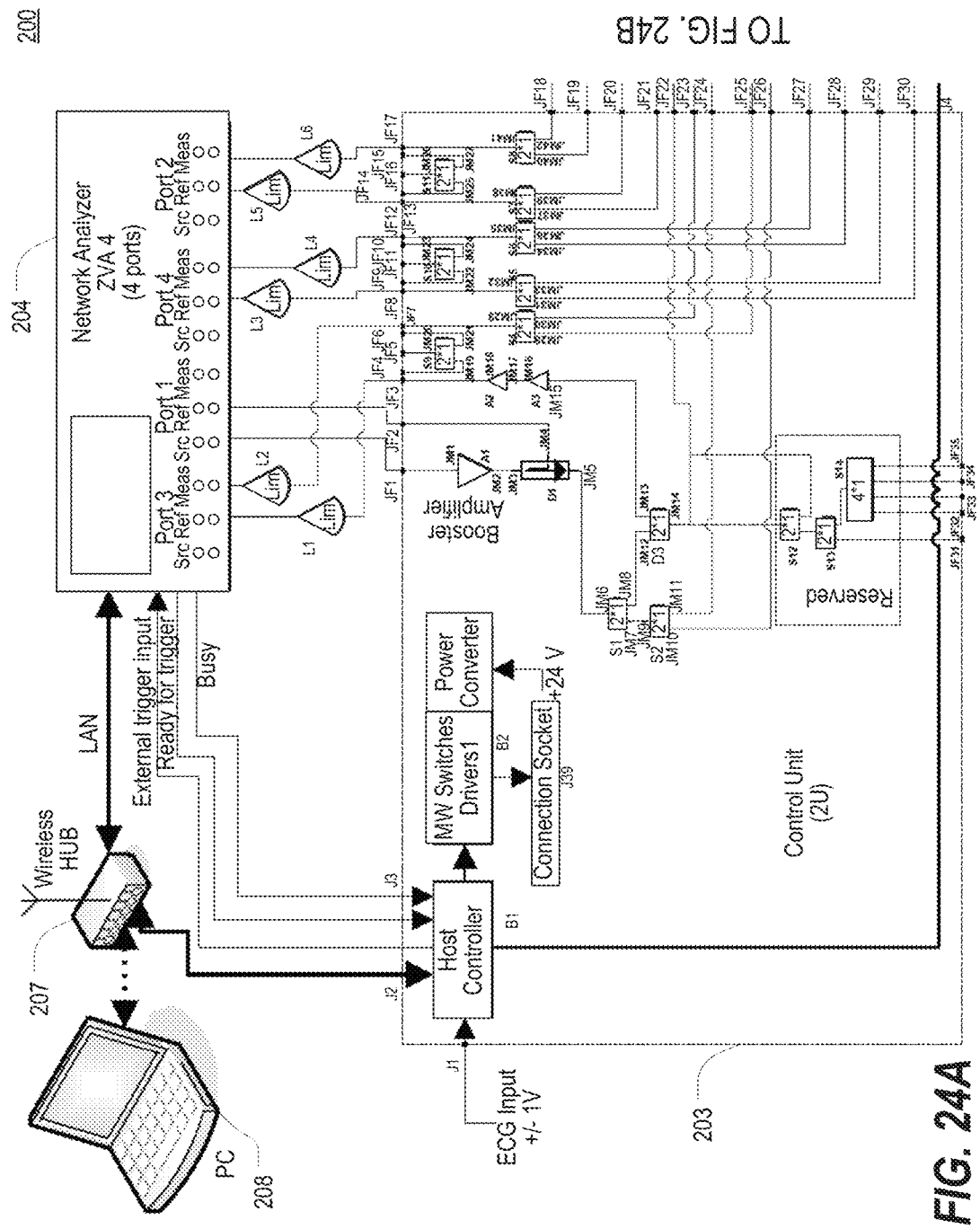
FIGS. 24A and 24B are a more detailed schematic diagram of the control system of FIG. 22.
Figure 24B:
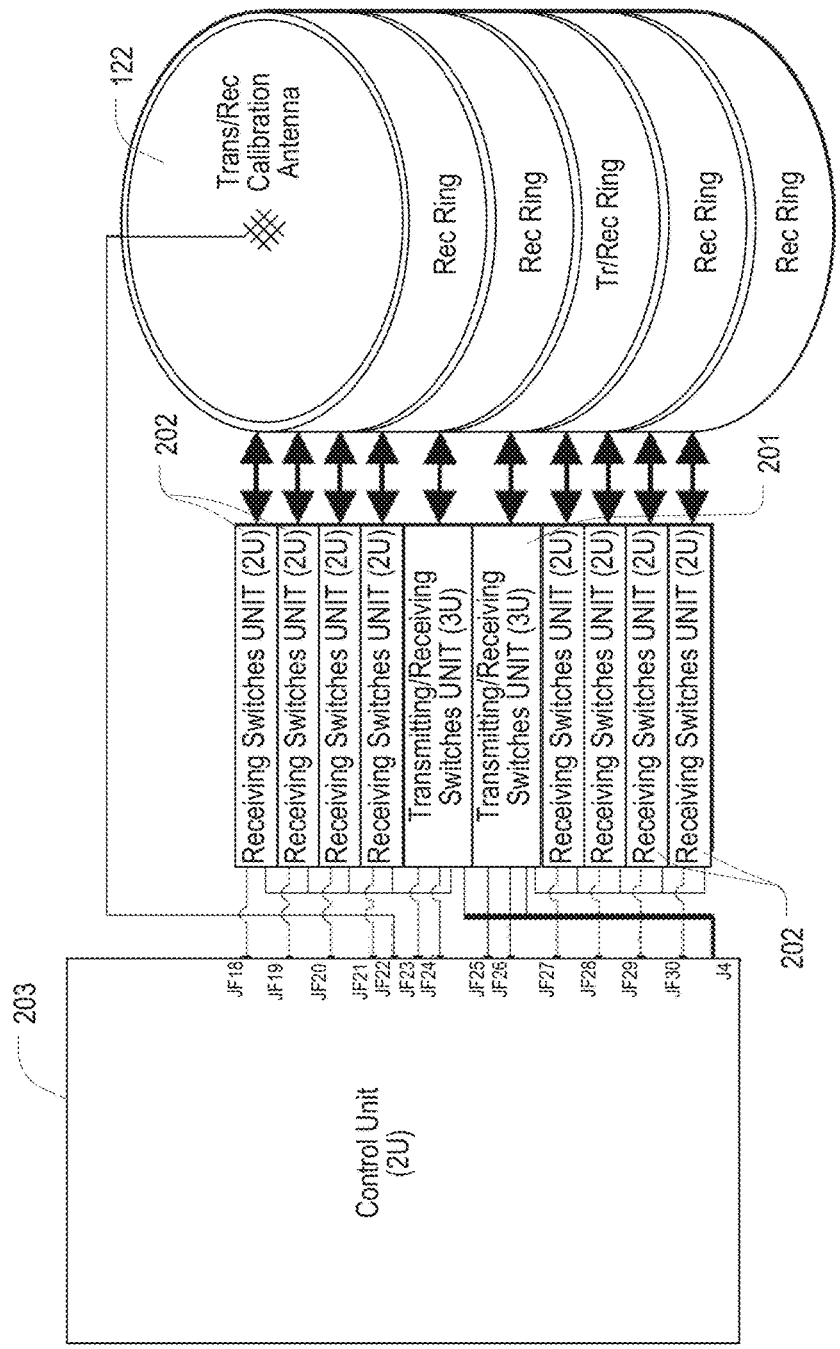

FIGS. 24A and 24B are a more detailed schematic diagram of the control system 200 of FIG. 22. As shown therein, the hub 207, which may provide both wireless and wired connections, communicatively connects the control unit 203, the network analyzer 204, and the user interface computer 208. The control unit 203 includes a host controller that interfaces with the hub 207 as well as provides a trigger input to the network analyzer 204 and receives "ready for trigger" and/or "busy" signals from the network analyzer 204. The host controller also receives an ECG input and controls drivers for MW switches. The control unit 203 also includes various circuitry, including amplifiers, multiplexers, and the like, to generate input signals for the ports of the network analyzer 204, which may be a ZVA 4 port vector network analyzer available from Rohde & Schwarz. The network analyzer 204 is also communicatively connected to the hub 207, preferably via a LAN, and operations of the control unit 203 and network analyzer 204 are under the control of the user interface computer 208. Power is supplied by a power converter which may receive 24V power from the power unit 205 as described elsewhere herein.

Figure 25:
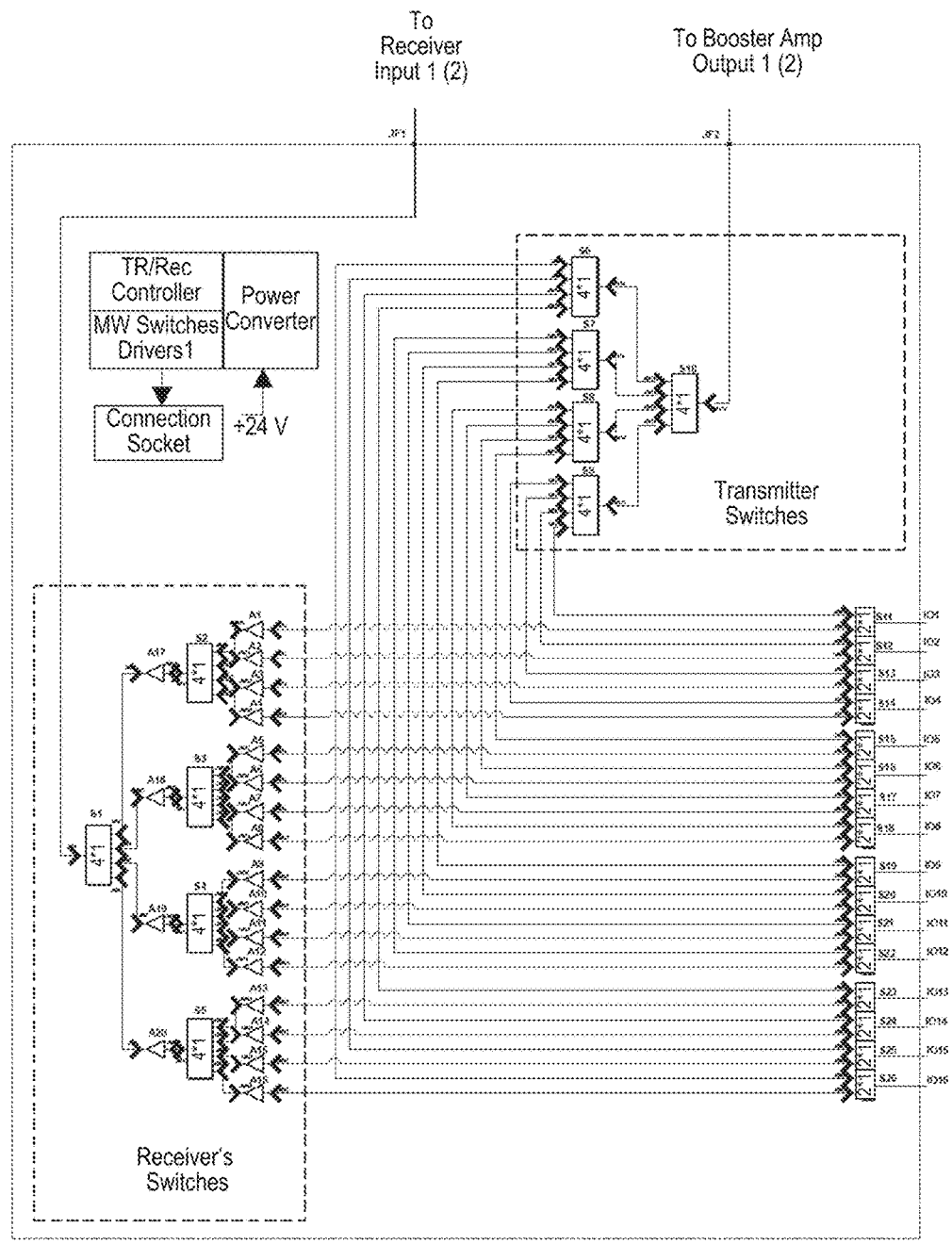
FIG. 25 is a schematic diagram of one of the transmitting/receiving switch units of FIG. 22.
Figure 26:
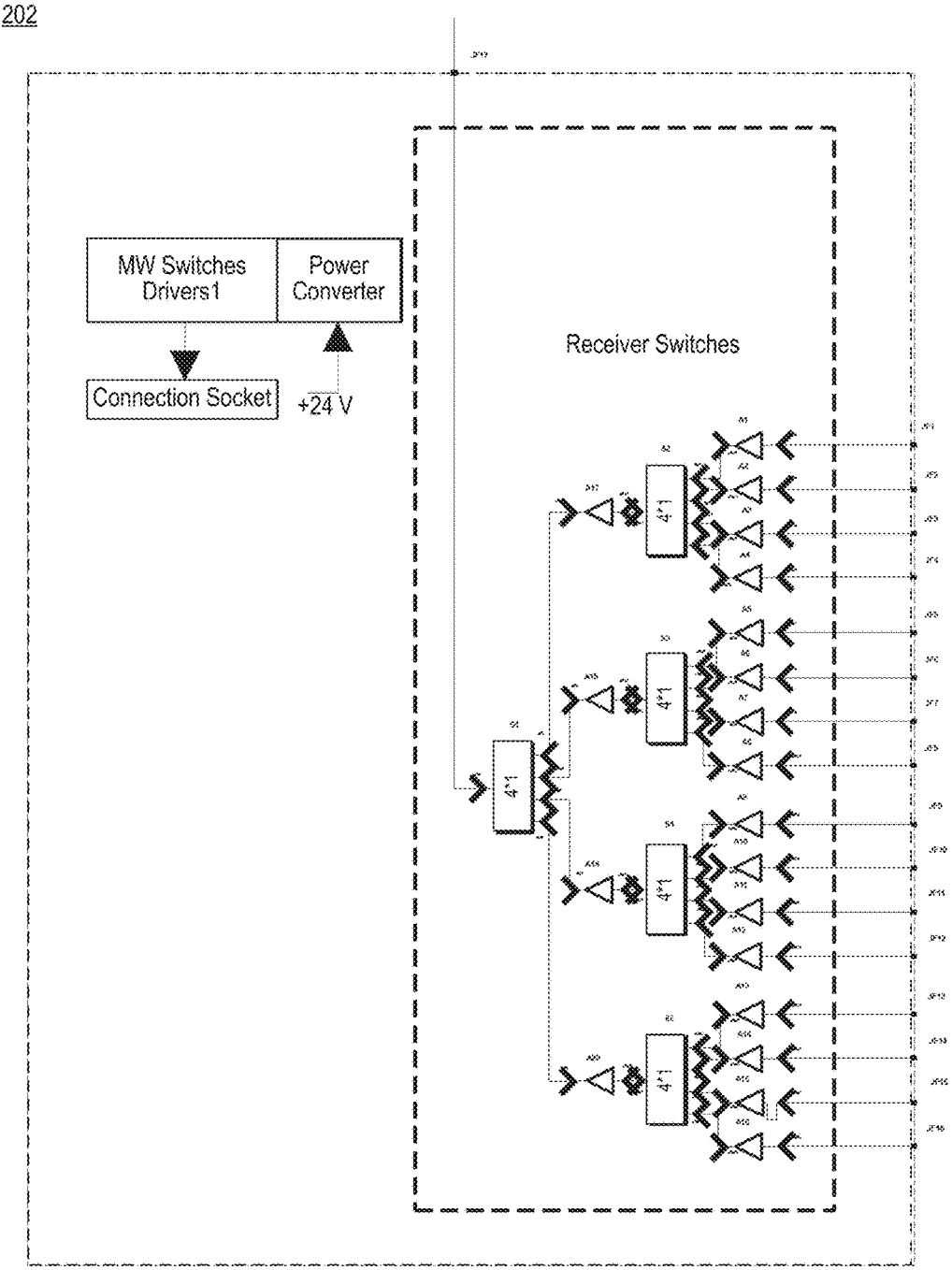
FIG. 26 is a schematic diagram of one of the receiving switch units of FIG. 22.
Figure 27:
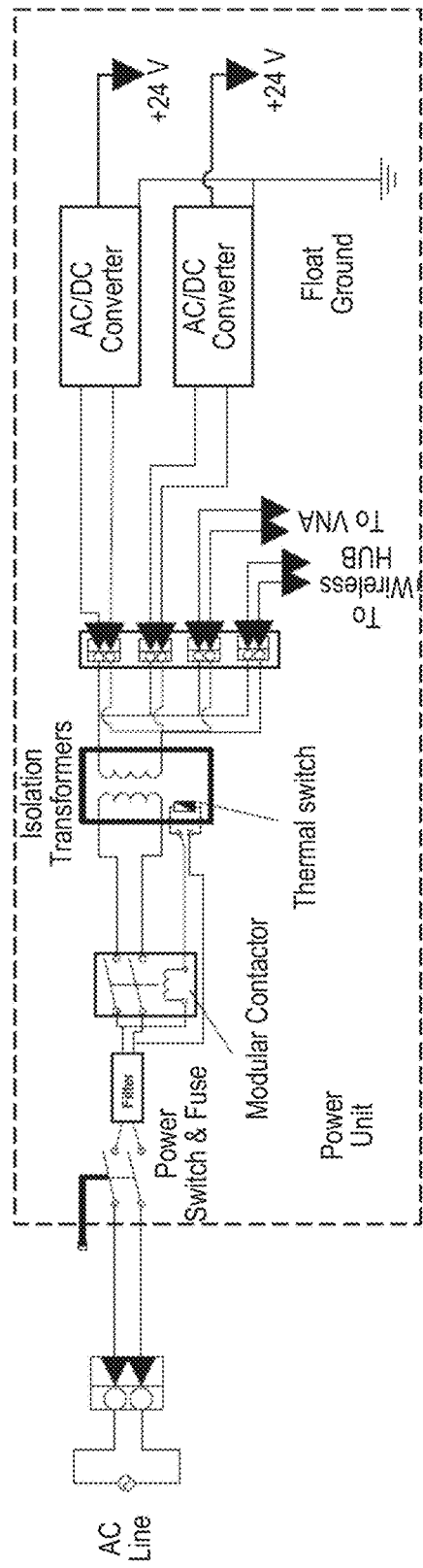
FIG. 27 is a schematic diagram of the power unit of FIG. 22.
Figure 28:
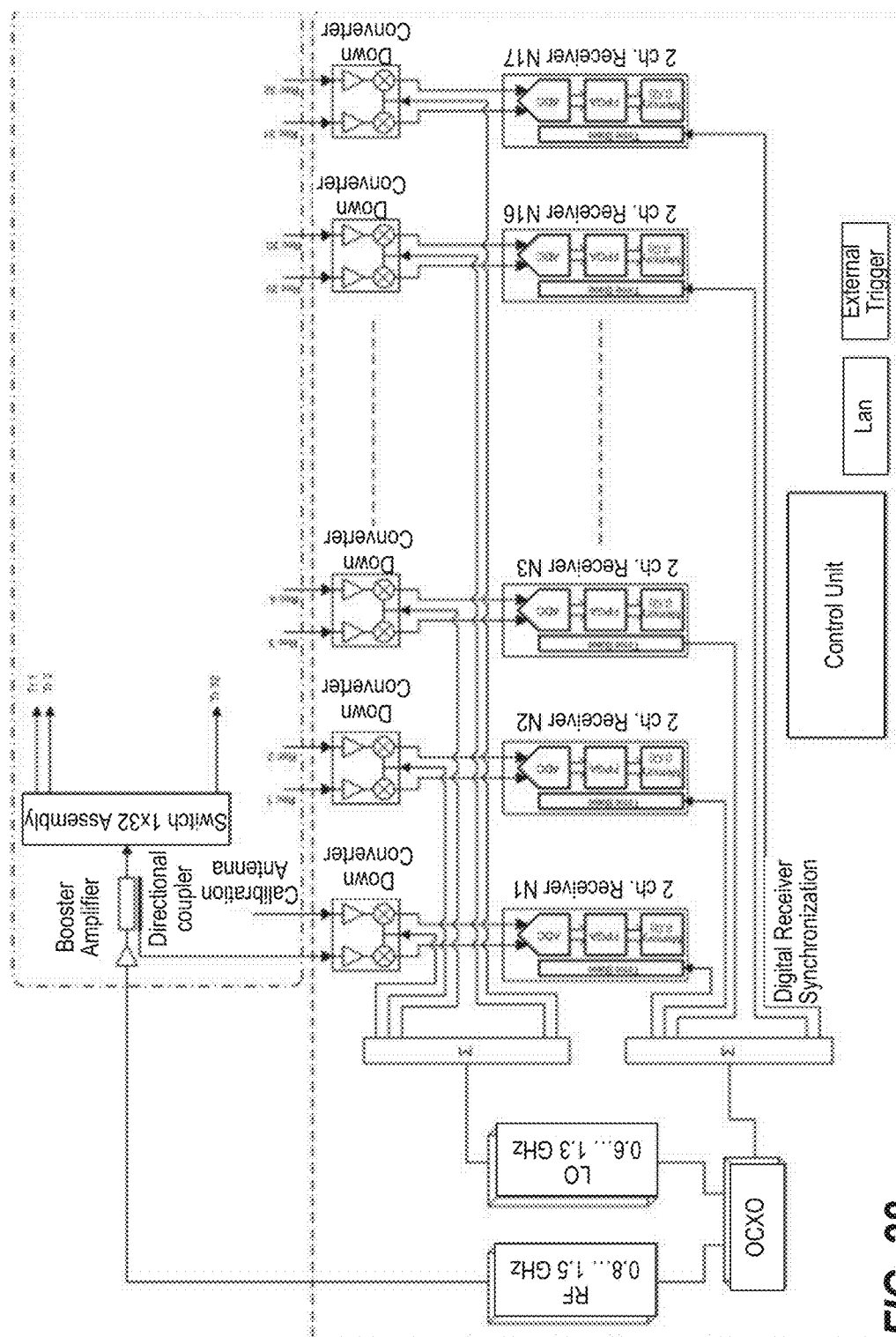
FIG. 28 is a schematic block diagram of additional or alternative details of a control system for the EMT system.

FIG. 25 is a schematic diagram of one of the transmitting/receiving switch units 201 of FIG. 22, and FIG. 26 is a schematic diagram of one of the receiving switch units 202 of FIG. 22. FIG. 27 is a schematic diagram of the power unit 205 of FIG. 22. As shown therein, the AC line input is converted into power for the hub 207, the network analyzer (VNA) 204, and for 24V AC/DC converters used to power the control unit 203 and transmitter/receiver and receiver switch units 201,202. FIG. 28 is a schematic block diagram of additional or alternative details of a control system for the EMT system 110.

In operation, a patient 15 is placed on his back on a patient support 120 and transported to the image chamber unit 131, shown in FIG. 9, or the image chamber unit 131 is transported to the location of the patient 15. For sanitary purposes, a single-use protective cap (not shown) may be placed over the patient's head 19. Such a protective cap may be made of plastic, latex, or the like. The patient's head 19 is then inserted into the entry opening 169 in the working chamber 122 as shown in FIG. 11. The headrest 118 may be adjusted as necessary or desired to arrange the patient's head in the desired position and orientation within the working chamber 122. The patient's head 19 bears against the membrane 133, which then conforms to the shape of the patient's head 19. With the patient's head 19 properly arranged, a technician fills the working chamber with a quantity of the prepared matching liquid. Filling may be carried out using the remote control of the pump, which in at least some embodiments has toggle switches to start and stop the pump, control the direction of flow (in or out), and flow rate. Filling is preferably initiated at a low flow rate to avoid splashing of matching liquid. Matching liquid is pumped into the working chamber until it is full, as shown in FIG. 15.

In addition to filling the working chamber with the matching liquid, the technician may also power on the various electronic components, including the control unit, the network analyzer, transmitter and receiver units, and the like. Using the user interface computer, software may then be utilized to calibrate and operate the system. Functionally, much of the operation of the EMT system 110 may be similar to that described in the aforementioned U.S. Pat. No. 7,239,731, U.S. Patent Application Publication No. 2012/0010493 A1 (U.S. patent application Ser. No. 13/173,078), and/or U.S. Patent Application Publication No. 2014/0276012 A1 (U.S. patent application Ser. No. 13/894,395), but various particular embodiments and features thereof may be described herein. Measurements are taken, a matrix of complex data is generated, and various algorithms are used to transform such data into tomographic images of the interior of the patient's head 19.

Figure 29:
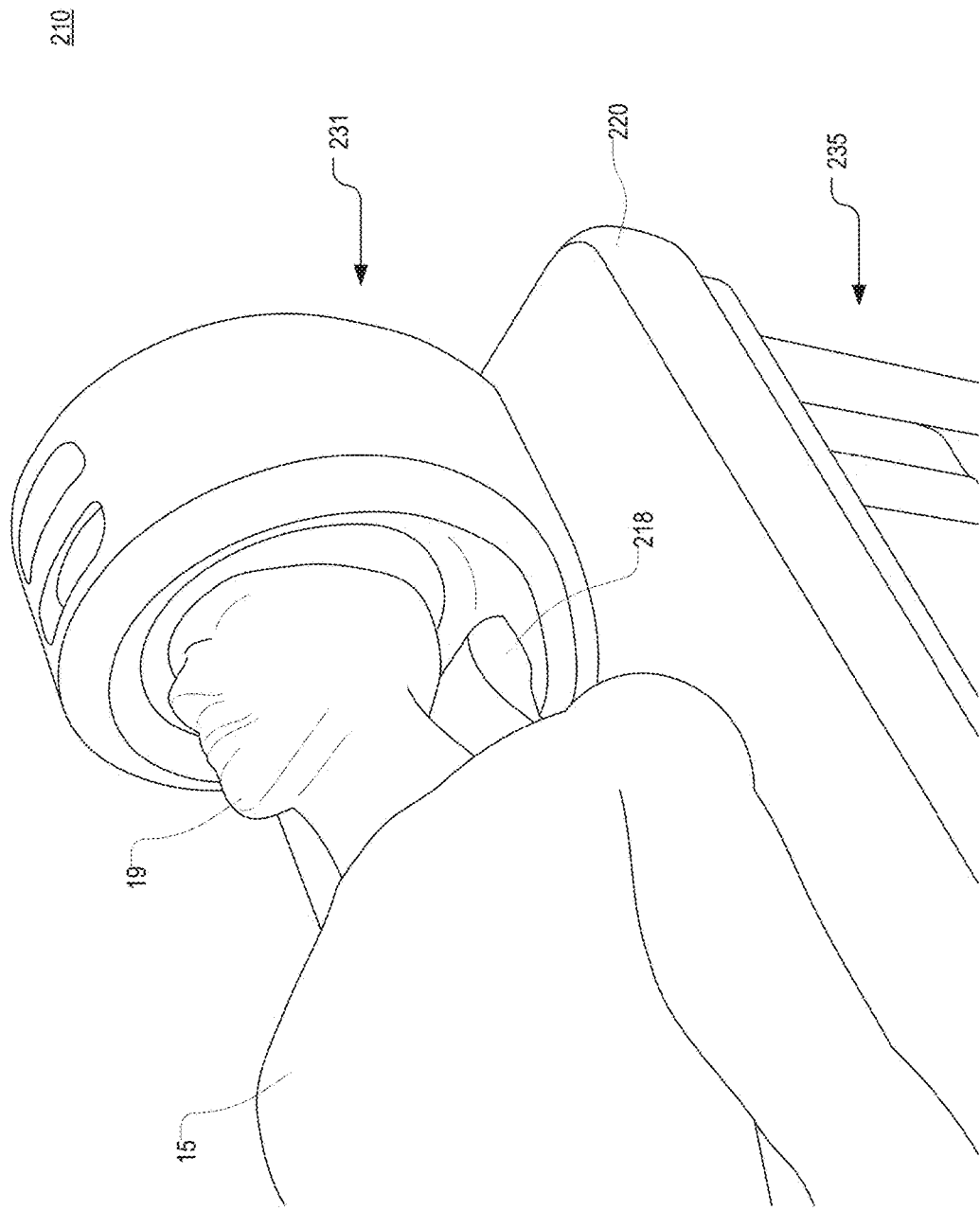
FIGS. 29 and 30 are a top front perspective view and a bottom rear perspective view, respectively, of another EMT system for imaging a human head in accordance with one or more preferred embodiments of the present invention.
Figure 30:
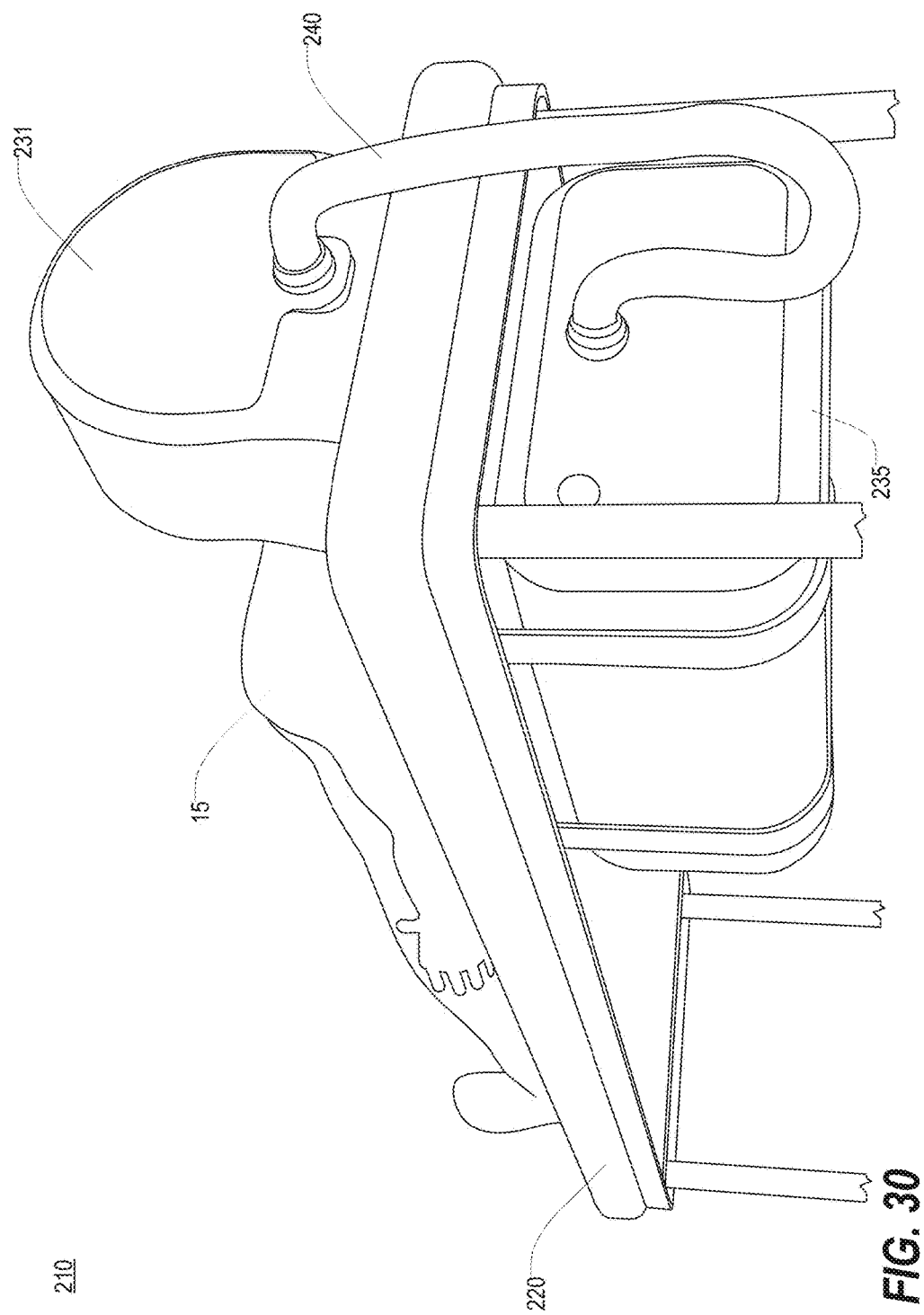

Other embodiments of the present invention are likewise possible. In particular, EMT systems having components that are more easily transported than those of the system 110 described hereinabove are possible without departing from the scope of the present invention. In this regard, FIGS. 29 and 30 are a top front perspective view and a bottom rear perspective view, respectively, of another EMT system 210 for imaging a human head 19 in accordance with one or more preferred embodiments of the present invention. The system 210 includes an image chamber unit 231, a control cabinet 235, and a hydraulic system 240 for supplying, circulating, and otherwise managing a matching fluid to the image chamber unit 231. The entire system 210 may be carried on a patient support 220, which again may be a gurney, cart, table, stretcher, or the like. In particular, the image chamber unit 231, which includes a built-in headrest 218, is carried on a top surface of the patient support 220, near one end, and the control cabinet 235 is carried beneath the patient support 220. Such a system 210 may be more conveniently transported, and in particular, the system 210 may be rolled with the patient support 220 onto and off of an ambulance and into a medical facility. In this regard, FIG. 31 is a top plan view of the system 210 in use in an ambulance 211.

Figure 32:
FIG. 32 is a side perspective view of a cap serving as a wearable image chamber unit in accordance with one or more preferred embodiments of the present invention.

In at least some embodiments, an image chamber unit of a type described herein is man-portable. As used herein, "man-portable" means cable of being carried or borne by one human. In particular, an image chamber unit of a type described herein may take the form of a wearable hat, helmet, cap, or the like. FIG. 32 is a side perspective view of a cap serving as a wearable image chamber unit in accordance with one or more preferred embodiments of the present invention. Aspects of such wearable apparatuses may be described, for example, in U.S. patent application Ser. No. 13/894,395.

Figure 31:
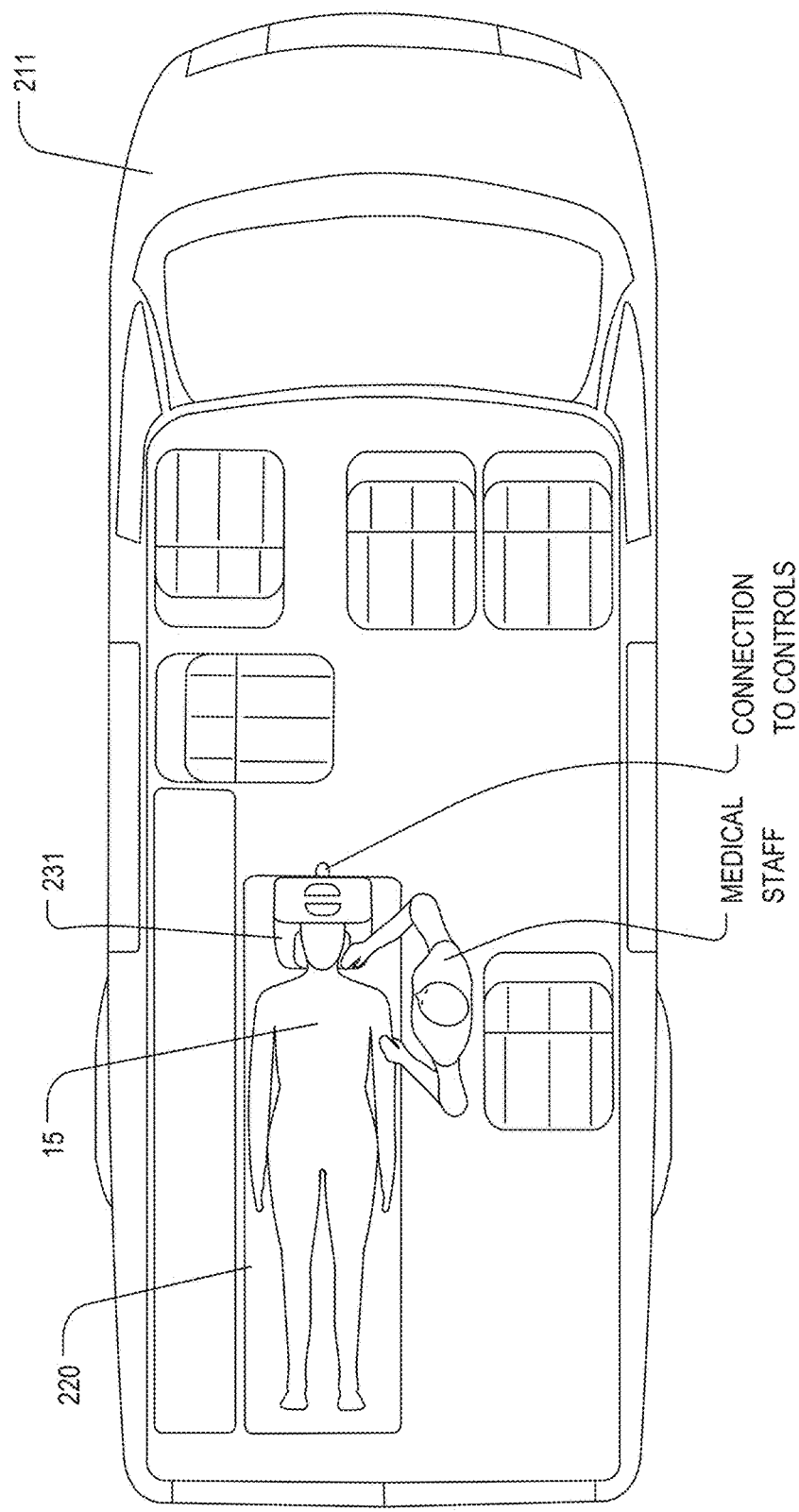
FIG. 31 is a top plan view of the system in use in an ambulance.
Figure 33:
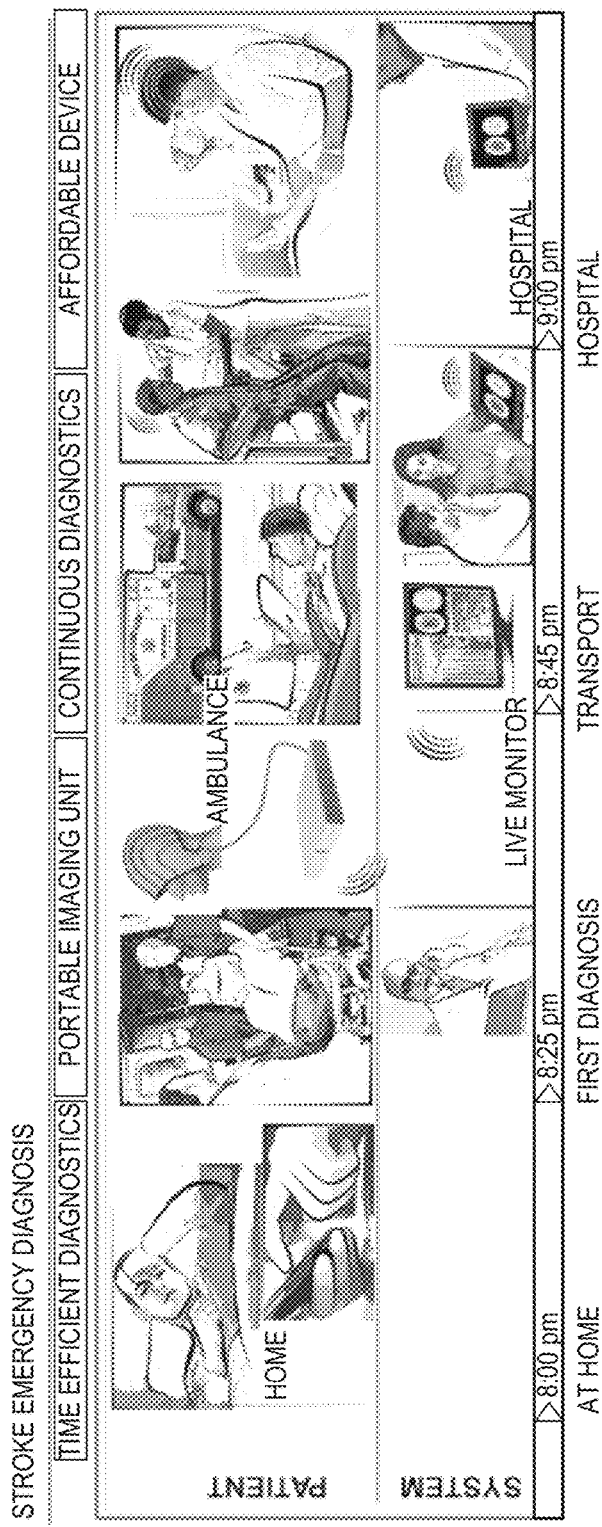
FIG. 33 is a pictorial illustration of a timeline for use of an EMT system, including the cap of FIG. 32, for imaging a human head in response to the onset of stroke symptoms in a patient.

At least some embodiments of the EMT systems presented herein, including without limitation the mobile embodiments such as the one presented in FIGS. 29-31 and the wearable cap of FIG. 32, may be utilized advantageously outside of the clinical setting. FIG. 33 is a pictorial illustration of a timeline for use of an EMT system, including the cap of FIG. 32, for imaging a human head in response to the onset of stroke symptoms in a patient. As shown therein, at 8:00 pm, a patient may be resting at home when he experiences the onset of stroke-like symptoms, such as disorientation and weakness in the face and arms. In response, he or a family member or friend contacts a medical provider, and an ambulance is dispatched. Meanwhile, a doctor or other medical practitioner is contacted and updated on the situation. The patient's head is placed in a mobile imaging unit, and scanning begins as shown around 8:25 pm. (In FIG. 33, the mobile image chamber unit is the cap of FIG. 32, but it will be appreciated that the unit of FIGS. 29-31 may be used instead.) Resulting data may be provided to the doctor, ambulance staff, imaging specialists, and other personnel. Some of the data may be used directly for diagnosis, treatment, or the like, while complex image-related data may be processed according to the systems and methods of the present invention to reconstruct images from which further diagnosis, treatment, or the like may be triggered. In at least some embodiments, such processing may generate an automatic alert that the data indicates that a potential stroke is likely. Notably, in at least some embodiments, such processing is carried out by a third party service provider who specializes in reconstruction of images according to the systems and methods of the present invention. During transport, from approximately 8:45 pm to 9:00 pm, the cap 331 continues to provide data regarding the patient's condition, and the local hospital staff is further updated and arranges and prepares for further treatment. Once the patient arrives at the hospital or other treatment center, the images and data may be used in providing timely, accurate information about the status of the stroke injury, and appropriate treatment and follow-up may be administered. Such a system could be utilized to provide the desired "under 3 hour" treatment that can make a major difference in the final outcome of the stroke injury and its affect on the patient.

It will be appreciated that in at least some embodiments, the systems, apparatuses and methods presented hereinabove may be incorporated into a 4D EMT differential (dynamic) fused imaging system. 4D EMT differential (dynamic) fused imaging system suitable for use with one or more preferred embodiments of the present invention are described in Appendix B.

Based on the foregoing information, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention.

Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements; the present invention being limited only by the claims appended hereto and the equivalents thereof.

What is claimed is:

1. A method of using an electromagnetic tomography (EMT) system to generate a data tensor for imaging a human head, comprimising:
   (a) in response to an emergency report and request from or on behalf of a stroke patient, providing an ambulance equipped with an image chamber unit for gathering measurement data pertaining to a human head in an electromagnetic tomography (EMT) system, the image chamber unit including:
  (i) an antenna assembly at least partially defining a horizontally-oriented imaging chamber and including an array of antennas arranged around the imaging chamber, the array of antennas including at least some transmitting antennas and at least some receiving antennas, and
  (ii) a housing, at least partially containing the antenna assembly, having a front entry opening into the imaging chamber, wherein a first interior portion of the imaging chamber is separated from a second interior portion of the imaging chamber such that the front entry opening is substantially liquid-sealed;
(b) positioning the stroke patient on his back on a patient support;
(c) inserting the head of the patient horizontally through the front entry opening of the image chamber unit and into the first interior portion of the imaging chamber;
(d) filling the second interior portion of the imaging chamber with a liquid;
(e) using a control system, causing the transmitting antennas to transmit a low power electromagnetic field that is received by the receiving antennas after passing through the patient's head in the imaging chamber and producing a data tensor from resulting signals that may be inversed to reconstruct a 3D distribution of dielectric properties within the human head and thereby to create an image of the patient's head;
(f) providing the data tensor to a hub computer system;
(g) producing EMT image results based on the provided data tensor; and
(h) providing the EMT image results to a medical practitioner at a treatment center for use in diagnosing or treating the stroke patient upon the patient's arrival at the treatment center.

2. The method of claim 1, wherein the liquid is a matching liquid for an electromagnetic tomography operation.

3. The method of claim 2, wherein the matching liquid is a mixture of glycerol, water and brine.

4. The method of claim 2, wherein the antenna assembly further includes a back disk attached to a rear of a plurality of antenna disks, and wherein the method further includes pumping the matching liquid into the second interior portion of the imaging chamber through at least one inlet in the back disk.

5. The method of claim 2, further comprising a step of positioning a catch basin adjacent the entry opening so as to receive liquid leaking from a front of the imaging chamber.

6. The method of claim 5, wherein the catch basin includes a drain tube.

7. The method of claim 1, further comprising a step of placing a sanitary protective cap over the patient's head to provide sanitary protection for the human head when it is inserted into the front entry opening.

8. The method of claim 1, wherein the step of filling the second interior portion with liquid is carried out after the step of inserting the head of the patient.

9. The method of claim 1, further comprising a step of carrying the image chamber unit on the patient support.

10. The method of claim 1, wherein the filling step is carried out using a hydraulic system.

11. The method of claim 10, further comprising a step of carrying the hydraulic system on the patient support.

12. The method of claim 1, further comprising a step of moving the patient support while the head of the stroke patient remains inserted in the front entry opening of the image chamber unit.

13. The method of claim 1, further comprising a step of carrying the control system on the patient support.

* * * * *